United States Patent [19]

Nagata et al.

[11] Patent Number: 4,705,852
[45] Date of Patent: Nov. 10, 1987

[54] 1-OXADETHIA CEPHALOSPORIN HYDROXAMIC ACID DERIVATIVES

[75] Inventors: Wataru Nagata, Hyogo; Tsutomu Aoki; Yasuhiro Nishitani, both of Osaka, all of Japan

[73] Assignee: Shionogi & Co., Ltd., Osaka, Japan

[21] Appl. No.: 876,976

[22] Filed: Jun. 20, 1986

Related U.S. Application Data

[62] Division of Ser. No. 576,404, Feb. 2, 1984, Pat. No. 4,614,797.

[30] Foreign Application Priority Data

Feb. 17, 1983 [JP] Japan .................................. 58-25940

[51] Int. Cl.[4] .................. C07D 205/08; A61K 31/535
[52] U.S. Cl. ..................................... 540/301; 540/300
[58] Field of Search .............. 540/30 D, 501; 514/210

[56] References Cited

U.S. PATENT DOCUMENTS 4,138,486  2/1979  Manisada et al. .................. 540/300

*Primary Examiner*—Nicholas S. Rizzo
*Attorney, Agent, or Firm*—Wenderoth, Lind & Ponack

[57] ABSTRACT

An antibacterial cephalosporin hydroxamic acid derivative represented by the following formula (I), processes for its preparation, compositions containing the same as an active ingredient, and a method for killing bacteria by contacting with said compound.

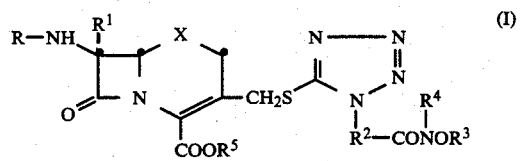

(wherein, R is acyl; $R^1$ is hydrogen or methoxy; $R^2$ is alkylene; $R^3$ is hydrogen, aliphatic group or a hydroxy-protecting group; $R^4$ is hydrogen or amino-protecting group; $R^5$ is hydrogen, light metal atom or carboxy-protecting group; and X is oxygen, sulfur, or sulfinyl).

7 Claims, No Drawings

1-OXADETHIA CEPHALOSPORIN HYDROXAMIC ACID DERIVATIVES

This is a divisional of Ser. No. 576,404, filed Feb. 2, 1984, now U.S. Pat. No. 4,614,797.

This invention relates to cephalosporin hydroxamic acid derivatives, especially 3-[1-(N-hydroxycarbamoylalkyl)-1H-tetrazol-5-ylthiomethyl]-substituted cephalosporin derivatives represented by the following formula (I):

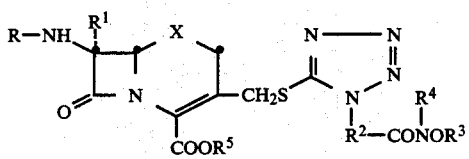

(wherein,
R is hydrogen or acyl;
$R^1$ is hydrogen or methoxy;
$R^2$ is alkylene;
$R^3$ is hydrogen, an aliphatic group, or a hydroxy-protecting group;
$R^4$ is hydrogen or amino-protecting group;
$R^5$ is hydrogen, light metal or carboxy-protecting group; and X is oxygen, sulfur, or sulfinyl).

In the above formula (I), the acyl represented by R is an acyl group of optionally substituted aliphatic, alicyclic, aromatic, araliphatic, heteroaromatic, or heterocyclic aliphatic carboxylic acid and preferably containing 1 to 20 carbon atoms in the target antibacterial compound (I). Acyl groups forming the amide side chain of natural or synthetic penicillins or cephalosporins are all included in this acyl. The following acyls are representative:

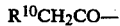 (1)

(wherein $R^{10}$ is an aliphatic, aromatic, heteroaromatic, or alicyclic group).

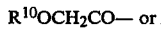 or (2)

wherein $R^{10}$ is the same as defined above (1).

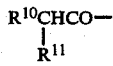 (3)

(wherein $R^{11}$ is optionally substituted or protected amino, carboxy, cyano, hydroxy, mercapto, or sulfo and $R^{10}$ is as defined above).

 (4)

(wherein $R^{12}$ is imino, oxo, thioxo, 1 to 10C optionally substituted hydroxyimino or alkylidene, or the like and $R^{10}$ is as defined above).

 (5)

 (6)

(wherein $R^{13}$ is mono- or dicyclic aromatic or heteroaromatic group).

Preferably, aliphatic $R^{10}$ is 1 to 5C optionally substituted alkyl, alkenyl, or alkynyl; aromatic $R^{10}$ is 1 to 12C optionally substituted phenyl, naphthyl, or the like; heteroaromatic $R^{10}$ is optionally substituted five or six membered monocyclic or dicyclic heteroaromatic group having oxygen, sulfur and/or up to 3 nitrogen as the heteroatom; and alicyclic $R^{10}$ can be a 4 to 6 membered, up to 2 unsaturated, and 3 to 5C optionally substituted cycloalkyl.

When $R^{11}$ is protected, the protection is for avoiding adverse change during synthesis or in animal bodies or for improving the physiological or pharmacological character of the compound.

Typical of the former $R^{11}$ include 1 to 8C alkyl (e.g., t-butyl, tetrahydropyranyl, tetrahydrofurayl), 1 to 8C alkenyl forming enol ether or enamine; 3 to 8C alkylated or alkoxylated silyl or stannyl; 7 to 20C aralkyl (e.g., trityl, substituted diphenylmethyl, phenacyl); 1 to 15C optionally substituted alkanoyl, alkenoyl, aroyl, carbonic acyl; and when $R^{11}$ is carboxy, optionally substituted alkyl, aralkyl, or aryl esters and amides are typical protective groups when it is deprotected without adverse effect on other part of the molecule.

Typical of the latter $R^{11}$ include sulfo, 1 to 8C optionally N-substituted carbamoyl or sulfamoyl, 1 to 20C carbalkoxy or carbaralkoxy, carboxy, cyano, 1 to 8C optionally substituted alkanoyl, monocyclic or dicyclic aralkanoyl, aroyl, or heterocyclic carbonyl. When $R^{11}$ is amino, the substituent can be 1 to 8C alkylsulfonyl, 1 to 8C alkylated oxoimidazolidinylcarbonyl, dioxopiperazinylcarbonyl, 1 to 8C alkylated ureidocarbonyl or thioureidocarbonyl.

Carboxy or sulfo as $R^{11}$ may be in a form of a 1 to 15C physiologically deprotectable ester.

Substituents of alkylidene as $R^{12}$ include aryl, halogen, carboxy, 1 to 20C esterified or amidated carboxy, 1 to 8C hydroxyalkyl, alkoxy, or the like, and each can be unsaturated or cyclized. Substituents of alkoxyimino $R^{12}$ include similar substituents. Optionally substituted typical mono- or di-cyclic aryl or heteroaromatic as $R^{13}$ has up to 12C and the second ring can be non-aromatic.

The groups $R^{10}$ to $R^{13}$ can be optionally substituted. Typical substituents are straight, branched, or cyclic carbon functions such as 1 to 20C alkyl, acyl, aralkyl, aryl, or heterocyclic groups (optionally substituted by e.g., alkyl, alkoxy, amino, carboxy, halogen,, hydroxy, oxo), carbamoyl, carboxy, cyano; up to 12C nitrogen functions (e.g., amino, acylamino, guanidyl, ureido, alkylamino, aralkylamino, isothiocyano, isocyano, nitro, nitroso); up to 12C oxygen functions (e.g., hydroxy, alkoxy, aralkoxy, aryloxy, heterocyclic oxy, oxo, cyanato, acyloxy); and the corresponding sulfur functions (e.g., sulfo, sulfamoyl); halogen; substituted silyl; or stannyl.

In the intermediates for synthesizing the objective antibacterials, R—NH— may be optionally protected amino (e.g., optionally substituted 1 to 20C alkylideneamino, aralkylideneamino, enamino, substituted silylamino).

Typical of alkylene $R^2$ is lower alkylene (e.g., 1 to 3C alkylene).

Typical of aliphatic group $R^3$ is a lower aliphatic group, especially 1 to 5C alkyl, alkenyl, or alkynyl. The hydroxyprotecting group $R^3$ includes alkoxyformyl, aralkoxyformyl, aralkyl (e.g., t-butoxyformyl, benzyloxyformyl, p-methoxybenzyl), or those described in J. F. W. McOmie: "Protective Groups in Organic Chemistry", Plenum Press, N.Y. (1973) and Flynn: "Cephalosporins and Penicillins", Academic Press, N.Y. (1972), etc. $R^3$ as acyl can be used for a physiological modification.

Amino-protecting group $R^4$ can be one of $R^3$ above.

Carboxy-protecting group $R^5$ is known in the penicllin and cephalosporin field and can be introduced or removed without adverse effect on other parts of the molecule.

The carboxy derivatives of Compound (I) are conventional amides, esters, salts, or the like of the carboxy. Thus, $R^5$ is either amide, ester, salt, or other derivative-forming group.

Typical examples of such groups are inorganic salts (e.g., lithium, sodium, potassium, magnesium, calcium, aluminum, or ammonium salt), organic base salts, for example, alkylamine salts (e.g., ethylamine, diethylamine, triethylamine, piperidine, morpholine, N-methylmorpholine salt), aromatic amine salts (e.g., aniline, dimethylaniline, naphthylamine salt), and aromatic base salts (e.g., pyridine, picoline, lutidine, nicotinamide, quinoline salt); physiologically acceptable salts, i.e., salts of light metals belonging to the 1st to 3rd groups and 2nd to 4th period of the Periodical Table (e.g., lithium, sodium, potassium, magnesium, calcium, aluminum); 1 to 8C aliphatic esters (e.g., methyl, ethyl, propyl, trichloroethyl, isopropyl, butyl, isobutyl, t-butyl, hexyl ester); 7 to 15C aralkyl ester (e.g., benzyl, methylbenzyl, dimethylbenzyl, methoxybenzyl, ethoxybenzyl, nitrobenzyl, aminobenzyl, diphenylmethyl, phthalidyl, phenacyl ester); 6 to 12C aromatic esters (e.g., diisopropylphenyl, indanyl, pentachlorophenyl, phenyl, trichlorophenyl ester); 3 to 12C silyl esters (e.g., trimethylsilyl, dimethylmethoxysilyl, t-butyldimethylsilyl ester); 3 to 12C stannyl esters (e.g., trimethylstannyl ester); 6 to 12C N-hydroxyamino ester (ester with e.g., acetone oxime, acetophenone oxime, acetaldoxim, N-hydroxysuccinimide, N-hydroxyphthalimide); physiologically acceptable esters, for example, monocyclic or dicyclic optionally substituted aryl esters (e.g., phenyl, xylyl, indanyl ester), 7 to 15C substituted aralkyl esters (e.g., phenacyl, phthalidyl ester), such substituted alkyl esters as 3 to 8C 1-alkanoyloxyalkyl (e.g., acetoxymethyl, propionyloxyethyl, pivaloyloxymethyl), 3 to 6C alkoxyformyloxyalkyl (e.g., 1-ethoxycarbonyloxyethyl), 2-alkenyl (e.g., 5-methyl-2-oxo-1,3-dioxol-4-en-4-ylmethyl), 2 to 8C alkoxyalkyl (e.g., methoxymethyl), substituted aralkyl (e.g., phenacyl ester, phthalidyl ester), or substituted aryl (e.g., phenyl ester, xylyl ester, indanyl ester) ester; acid anhydride, i.e., symmetric anhydride or unsymmetric anhydride with inorganic acid (e.g., carbonic acid, phosphoric acid, sulfuric acid, sulfurous acid) or such 1 to 12C organic acid as carboxylic acid (e.g., alkoxyformic acid, acetic acid, propionic acid, valeric acid, benzoic acid), 1 to 12C sulfonic acid (e.g., methanesulfonic acid, ethanesulfonic acid, benzenesulfonic acid, mesitylenesulfonic acid), or the like; and substituted removable amides and hydrazides, being $OR^5$ of anequivalent effect.

The said protective part may further be substituted. It is absent in the target compound. So, the structure can vary widely as far as the protection and deprotection are possible.

In above definitions, alkyl part is optionally substituted straight, branched, or cyclic alkyl.

The acyl part can be optionally substituted straight, branched, or cyclic alkanoyl, mono- or di-cyclic aroyl, aralkanoyl, arylalkenoyl, alkylsulfonyl, arylsulfonyl, carbamoyl, carbalkoxy, carbaralkoxy, or the like.

The aryl part is mono- or di-cyclic and 5- or 6-membered aryl optionally having a substituent or hetero atom selected from 1 to 3 nitrogen atoms, oxygen, and/or sulfur in the nucleus. Typical heteroaromatic groups include furyl, thienyl, pyrrolyl, oxazolyl, isoxazolyl, thiazolyl, isothiazolyl, imidazolyl, oxadiazolyl, thiadiazolyl, triazolyl, thiatriazolyl, tetrazolyl, pyrazinyl, pyridazinyl, pyridyl, pyrimidyl, triazinyl, benzofuryl, indolyl, isoquinolinyl, purinyl, pyrimidopyridyl, and quinolinyl.

Typical substituents for the above radicals include acyl, acylamino, acyloxy, alkoxy, alkyl, alkylthio, aralkoxy, aralkyl, aryl, aryloxy, arylthio, amino, carbamoyl, carboxamide, carboxy, protected carboxy, cyano, dialkylamino, formimidoylamino, halogen, hydroxy, nitro, oxo, and the like.

Cephalosporins having 3-carbamoylalkyltetrazolythiomethyl are known (U.S. Pat. No. 4,286,089; Jap. Pat. Appln. Kokai No. 52-83,873), but Compounds (I) being hydroxamates are unknown.

Compounds (I) are stable and superior to other drugs in their antibacterial activity and in their pharmacological characters (e.g., absorption, distribution, excretion, metabolism, disulfiram-like side reaction). Especially long and high blood level and anti-Gram-positive activity are remarkable.

Compounds (I) are antibacterials against aerobic Gram-positive bacteria (e.g., *Bacillus cereus, Bacillus subtilis, Corynebacterium diphtheriae, Staphylococcus aureus, Streptococcus pyrogenes, Streptococcus pneumoniae, enterococci*) and Gram-negative bacteria (e.g., *Enterobacter cloacae, Escherichia coli, Klebsiella pneumoniae, Proteus mirabilis, Proteus morganii, Proteus rettgeri, Proteus vulgaris, Salmonella paratyphi, Salmonella typhi, Serratia marcescens, Shigella sonnei*), and anaerobic bacteria (e.g., *Bacteroides fragilis, Eubacterium lentum*), and thus they are useful as bacteriocidal, bacteriostatic, disinfectant, or antiperishable agents. They are useful as bacterial growth inhibitors on human, animal, plant, or perishable subjects, or as human or animal growth promoting additives in foodstuff.

For example, they are useful for treating or preventing human, veterinary, or poultry infections caused by sensitive Gram-positive bacteria or Gram-negative bacteria or some anaerobic bacteria.

This invention also provides a method for treating or preventing human or veterinary bacterial infections (e.g., abscess, bronchitis, dermatitis, ear infections, empyema, enteritis, gastroenteritis, nasopharyngitis, osteomyelitis, pneumonitis, pneumonia, pustulosis, pyelonephritis, respiratory tract infection, rhinitis, septicemia, tonsillitis, ulceration, urinary tract infection, wound and soft tissue infection) caused by sensitive bacteria by administering an effective amount of Compound (I), e.g., at a typical daily dose of 10 micrograms to 1 gram externally, 0.2 to 5 gram intravenously, or 1 to 2 gram orally at an interval of 3 to 12 hours depending on the infecting bacteria and condition of the patient, if required formulating with a conventional additive.

Compound (I) as a carboxylic acid or its light metal salt may be used intravenously, intramuscularly, or subcutaneously (e.g., ampoule or vial containing crystals, lyophilizate, or powder) or orally, if required in admixture with an excipient. A pharmacological ester can be used orally (e.g., capsule, dry syrup, dispersion, emulsion, granules, powder, solution, suspension, syrup, tablet, troches), externally, or topically (e.g., ear, nasal, or ocular drug, ointment, powder, spray, suppository).

Compounds (I) are also useful as starting materials for synthesizing other antibacterials or for testing sensitivity of bacteria to the antibacterial (I).

Compounds (I) are useful in various oral or parenteral dosage forms solely or mixed with other coacting substances. The pharmaceutical compositions may contain 0.01 to 99% of Compound (I) dissolved, dispersed, or suspended in a solid or liquid pharmaceutical carrier.

The compositions are solid preparations (e.g., capsule, dry syrup, granule, pellet, pill, powder, suppository, troche, tablet, vial), liquid preparations (e.g., ampoule, dispersion, elixir, emulsion, inhalant, injection, ointment, solution, suspension, syrup), or the like. They can be flavored or colored, and capsules, granules, and tablets may be coated. They can be in a unit dosage form.

The carriers are harmless to both Compound (I) and patients and include, for solids, binders (e.g., acacia, carboxymethylcellulose, gelatin, glucose, polyvinylpyrrolidone, sodium alginate, sorbitol, starch, syrup, tragacanth), bulking agents (e.g., bentonite, calcium carbonate, calcium phosphate, glycine, kaoline, lactose, polycarboxymethylene, salt, sorbitol, starch, sugar, talc), diluents (e.g., calcium carbonate, kaolin, lactose, starch, sucrose), disintegrators (e.g., agar, carbonates, sodium laurylsulfate, starch), lubricants (e.g., boric acid, cacao oil, magnesium stearate, paraffin, polyethylene glycol, silica, sodium benzoate, stearic acid, talc), or wetting agents (e.g., hydroxypropyl cellulose); for solutions, solvents (e.g., alcohol, buffer, methyl oleate, peanut oil, sesame oil, water), emulsifying agents (e.g., acacia, lethicin, sorbitan monooleate), suspending agents (e.g., aluminum stearate gel, carboxymethyl cellulose, gelatin, glucose, hydrogenated fats, hydroxyethylcellulose, methyl cellulose, sorbitol, sugar syrup), buffers, dispersing agents, or solubilizing agents; and for both, preservatives (e.g., methyl or ethyl p-hydroxybenzoate, sorbic acid), absorption promoters (e.g., glycerin mono- or di-medium sized alkanoates), antioxidants, aromatic substances, analgesics, edible coloring agents, stabilizing agents, or like.

Compounds (I) are synthesized, for example, as follows:

(1) Salt formation

Compound (I) having free carboxy forms a salt by neutralizing with an organic or inorganic base or by exchange decomposition with a salt of weak acid (e.g., carbonic acid, weak carboxylic acid) conventionally (e.g., by neutralizing the free acid with light metal hydroxide, carbonate, or hydrogencarbonate, or by treating with carboxylate salt) in a polar organic solvent (e.g., alcohol, ester, ketone), and then adding less dissolving solvent. The reaction time is usually 1 to 10 minutes at lower than 50° C.

Antibacterial salts as solid (e.g., crystals, powders) are made by crystallizing, precipitating, filtrating, or lyophilizing. Separating of a salt from a solution purifys the product.

(2) Deprotection of protected carboxy

Deprotection of protected carboxy gives the parent Carboxy compound (I), by a conventional method, e.g., as follows:

(a) Highly reactive, amide, anhydride, and ester type protecting groups are removed with an aqueous acid, base, buffer solution, or ion exchange resin. Some insufficiently reactive esters (e.g., p-nitrobenzyl, phenacyl, trichloroethyl ester) are deprotected after activating by reducing (e.g., with acid and metal, dithionate, or hydrogen).

(b) Aralkyl and 2-haloalkyl ester type protecting groups (e.g., benzyl, methylbenzyl, dimethylbenzyl, nitrobenzyl, diphenylmethyl, triphenylmethyl, haloethyl ester) are removed by hydrogenating over a catalyst (e.g., nickel, palladium, platinum).

(c) tert.-Alkyl, cyclopropylalkyl, alkylsulfonylalkyl, aralkyl, etc. ester type protecting groups (e.g., t-butyl, cyclopropylmethyl, cyclopropylethyl, methylsulfonylethyl, benzyl, alkylbenzyl, alkoxybenzyl, diarylmethyl, trityl ester) are removed by hydrolyzing or solvolyzing (e.g., with Lewis acid, mineral acid, strong carboxylic acid, sulfonic acid), if required in the presence of a cation scavenger (e.g., anisole, dimethylsulfide, thiophenol).

(d) Alkenyl, hydroxyaralkyl, phenacyl, or the like ester type protecting groups (e.g., vinyl, ethynyl, p-hydroxy-3,5-di-t-butylbenzyl, phenacyl, halophenacyl esters) are removed with a base or nucleophilic reagent. Photochemically reactive phenacyl ester protections can be removed by irradiation.

(e) and other various carboxy deprotections.

(2a) Deprotection of protected hydroxy

Typical deprotections of protected hydroxy giving the corresponding free hydroxy are as follows:

(a) Highly reactive ester-type protecting groups (e.g., haloalkanoyl) are removed with an aqueous base.

(b) Alkoxycarbonyl, aralkoxycarbonyl, and the like carbonate-type protecting groups can be removed with an acid (e.g., mineral acid, Lewis acid, strong carboxylic acid) at $-50°$ C. to 50° C., optionally in the presence of a cation scavenger.

(c) Acetal, enol ether, trialkylsilyl, t-alkyl, and the like ether-type protecting groups are removed with an acid.

(3) Protection of reactive functions

When Compound (I) is subjected to a chemical reaction to make other Compound (I), reactive functional groups other than the objective group are conventionally protected previously.

Typical protection reactions are, e.g., acylation and etherification for hydroxy; e.g., acylation, enamine formation, and silyl introduction for amino; and e.g., amidation, acid anhydride formation, and esterification for carboxy. Physiologically active ester formation is one example of this type of protection.

Carboxy Compound (I) or its reactive derivative, for example, salt or mixed anhydride with acid (e.g., carbonic acid, carboxylic acid, mineral acid including hydrogen halides, or sulfonic acid) gives the corresponding ester by the action of alcohol or its reactive derivative (e.g., diazo compound or chloride, bromide, iodide, sulfonate). The reaction usually requires a condensing reagent as referred to in the section on amidation with carboxylic acid or an acid scavenger as referred to in the section on amidation with acid anhydrides.

These protection and deprotection methods for reactive groups are disclosed in J. F. W. McOmie Ed., "Protective Groups in Organic Chemistry", pp. 183 (1973), Plenum Press, N.Y.; S. Patai Ed., "The Chemistry of Carboxylic acids and Esters" in "The Chemistry of Functionsl Groups", pp 505 (1969), Interscience Publ., John Wiley & Sons, Ltd., London; and S. Patai Ed., "The Chemistry of Carboxylic acids and Esters" in a series of "The Chemistry of Functional Groups", pp 505 (1969), Interscience Publ., John Wiley & Sons, Ltd., London; and various patent literature. (4) Amidation.

A reaction of Amine (II) or its reactive derivative with Acid (III) or its reactive derivative gives Amide (I) or its derivative.

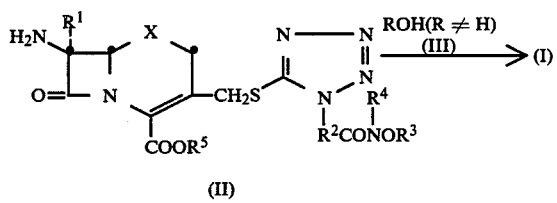

(II)

Typical reactive derivatives of Amine (II) have the 7-amino activated by silyl (e.g., trimethylsilyl, methoxydimetylsilyl, t-butyldimethylsilyl), stannyl (e.g., trimethylstannyl), alkylene as a part of the enamino of the amino with a carbonyl compound (e.g., aldehyde, acetone, acetylacetone, acetoacetate, acetoacetonitrile, acetoacetanilide, cyclopentanedione, acetylbutyrolacetone), 2 to 12C alkylidene (e.g., alkylidene, 1-alkoxyalkylidene, 1-alkoxy-1-phenoxyalkylidene, 1-haloalkylidene), 7 to 12C aralkylidene (e.g., aralkylidene, 1-haloaralkylidene), acid as a salt of the amino (with e.g., carboxylic acid, mineral acid, sulfonic acid), or the like, and that protected at other functions of the molecule.

The reactive derivatives of Acid (III) include acid anhydride, halide, reactive ester, reactive amide, azide and other conventional derivatives for acylation.

The procedures of the above amidation are, e.g., as follows:

(a) Free acid (III) is used in the presence of a condensing reagent [carbodiimide (e.g., N,N'-diethylcarbodiimide, N,N'-dicyclohexylcarbodiimide), carbonyl compound (e.g., carbonyldiimidazole), isoxazolinium salt, acylamino compound (2-ethoxy-1-ethoxycarbonyl-1,2-dihydroquinoline), or the like]. Preferably, Amine (II) or its reactive derivative, 1 to 2 molar equivalents of the condensing reagent, and 1 to 2 molar equivalent of Acid (III) or mixed at 0° C. to 70° C. for 1 to 5 hours preferably in an aprotic solvent (e.g., halohydrocarbon, nitrile, ether, amide solvent or the mixture).

(b) Acid anhydride—This is a symmetric anhydride, intramolecular acid anhydride (e.g., isocyanate, ketene), or mixed anhydride with a mineral acid (e.g., carbonic half ester, hydrohalogenic acid, phosphoric acid, sulfuric acid) or organic acid (e.g., alkanoic acid, aralkanoic acid, sulfonic acid) of Acid (III). Preferably, Amine (II) or its reactive derivative, 1 to 2 molar equivalents of the acid anhydride, and 0 to 10 molar equivalent of an acid scavenger [for example, inorganic base (e.g., oxide, hydroxide, carbonate, or hydrogen carbonate of alkali metal or alkaline earth metal), organic base (e.g., 3 to 12C tertiary amine, 5 to 12C aromatic base), oxirane (e.g., 2 to 8C alkylene oxide, 8 to 12C aralkylene oxide), pyridinium salt (e.g., tripyridiniumtriazine trichloride), adsorbent (e.g., Celite), or the like] are mixed at −30° C. to 80° C. for 10 minutes to 7 hours preferably in an aprotic solvent (e.g., halohydrocarbon, nitrile, ether, amide, or a mixture).

(c) Acid halide—This is chloride, bromide, or iodide of Acid (III). Preferably, Amine (II) or its reactive derivative, 1 to 2 molar equivalents of the acid halide, and 1 to 10 molar equivalents of said acid scavenger are mixed at −30° C. to 80° C. for 10 minutes to 7 hours in a solvent (e.g., halohydrocarbon, nitrile, ether, ester, ketone, water, dialkylamide, or a mixture).

(d) Reactive ester—This is a 2 to 6C enol ester (e.g., vinyl ester, isopropenyl ester), 6 to 12C aryl ester (e.g., phenyl ester, halophenyl ester, nitrophenyl ester), 5 to 6-membered heterocyclic ester (e.g., 1-hydroxybenzotriazole ester), ester with N-hydroxy compound, diacylhydroxylamine ester; thioester; or the like conventional reactive ester. This is handled as set forth below. An enzymatically reactive ester (e.g., 1 to 5C alkyl ester, oligoethyleneglycol ester) may conventionally be used in an aqueous solvent in the presence of an amidase.

(e) Reactive amide—This is an aromatic amide (e.g., amide with 2-ethoxy-1,2-dihydro-quinoline, imidazole, triazole), diacylanilide, or the like amide of Acid (III) handled as given below.

(f) Formimino compound (e.g., N,N-dimethylformimino ester halide) of Acid (III) is handled as given below.

The reactions from (d) to (f) are usually carried out by mixing 1 molar equivalent of Amine (II) or its reactive derivative, 1 to 2 molar equivalents of Acid (III) or its reactive derivative at −20° C. to 40° C. for 1 to 5 hours in 2 to 20 parts by weight of an aprotic solvent (e.g., halohydrocarbon, ether, ketone, ester, nitrile, amide, or a mixture).

(5) Introduction of the 3-substituent

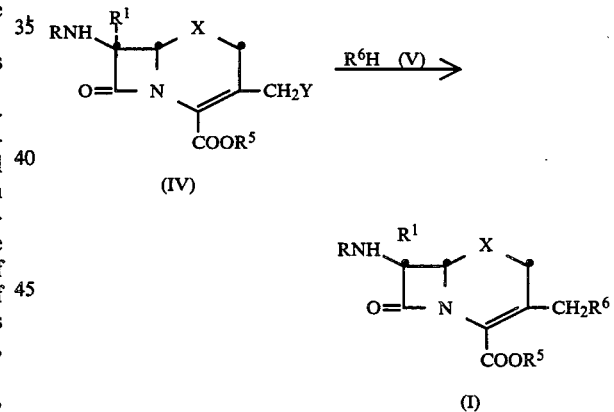

Compound (IV, Y=leaving group) is treated with a heteroaromatic thiol (V, R=heterocyclic thio) or its reactive derivative giving an objective Compound (I, R is as above). Reactive alkanoyloxy, halogenated alkanoyloxy, halogen, sulfonyloxy, and the like are typical Y. Alkali metal, alkaline earth metal, ammonium, organic base, and the like salts are typical reactive derivatives of Thiol (V).

Compound (IV, Y=hydroxy) is treated with carboxylic acid (V, R=acyloxy) or its reactive derivative giving an objective Compound (I, R=acyloxy). Halide, anhydride, etc., are typical reactive derivatives.

Compound (IV, Y=leaving group) is treated with a reactive aromatic base (V) to give the objective Compound (I) where R is onium (e.g., pyridinium, carbamoylpyridinium, or bicyclic, or tricyclic pyridinium derivatives, etc.).

The reaction proceeds at −20° C. to 60° C. even in an anhydrous or aqueous solvent (e.g., halohydrocarbon, ether, ketone, amide, or a mixture). This reaction is promoted by a dehydrohalogenating reagent (e.g., phosphoryl chlorides, thiocyanate).

(6) Methoxylation

A compound of the formula (I) having 7-hydrogen is treated with an N-halogenating reagent, dehydrohalogenating reagent, and methanol, successively to give the corresponding 7β-amido-7α-methoxy Compounds (I) from either 7α- or 7β-hydrogen compound.

Thus 7-hydrogen compounds are, for example, handled as follows:

(a) Reacting with alkyl hypohalite (e.g., t-butyl hypochlorite) and alkali metal methoxide (e.g., lithium methylate, sodium methylate) in methanol;

(b) Reacting with molecular halogen and a base (e.g., DBU, picoline, triethylamine, metal alkoxide—lithium methoxide, sodium methoxide, magnesium methoxide, etc.—) in methanol.

(c) Reacting with N-haloamide, N-haloimide, hypohalite ester, hypohalite salt, or the like, a dehydrohalogenating reagent (e.g., alkali metal alkoxide, aryl alkali metal), and then methanol.

(d) Alkylsulfenylamino formation and substitution by methoxy.

(e) 7-Alkylsulfenyl introduction and substitution by methoxy.

(7) Modifying other functions

In Compounds (I), any other functional groups may be modified, protected, or deprotected conventionally in a manner known to those skilled in the art.

Oxacephem ring formation by the action of a base on the corresponding 3-leaving group is also a reaction of this type. (Reaction conditions)

The reactions from (1) to (7) are usually carried out under conditions, further to those specifically given above, at −50° C. to 100° C., preferably at −20° C. to 50° C. for 10 minutes to 5 hours, if required in a dried and stirred solvent. Reaction time may be longer, unless any side reaction occurs.

Typical reaction solvents are, in addition to those cited before, one of hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, diglyme, dioxane, tetrahydrofuran), ketone (e.g., acetone, methyl ethyl ketone, cyclohexanone, ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethyl phosphorotriamide), sulfoxide (e.g., dimethyl sulfoxide), carboxylic acid, (e.g., formic acid, acetic acid, propionic acid, valeric acid), organic base (e.g., diethylamine, triethylamine, pyridine, picoline, collidine, quinoline), alcohol (e.g., methanol, ethanol, propanol, hexanol, octanol, benzyl alcohol), water, ammonia, and other industrial solvents and a mixture thereof.

The products are obtained from each reaction mixture by removing contaminants (e.g., by-products, solvents, unreacted starting materials) conventionally (e.g., by concentrating, extracting, washing) and purified by usual work up (e.g., adsorbing, distilling, eluting, filtrating, precipitating).

Following examples illustrate the embodiments of this invention.

Physicochemical constants of the products are summarized in Table 1 at the end of Examples. In the Examples, "part" shows part by weight and "equivalent" shows molar equivalent to the starting betalactam. Values of IR show frequency in $cm^{-1}$, NMR show chemical shifts in ppm, and J show coupling constant in cps.

(Abbreviations)

BH is for diphenylmethyl, Cbz is for carbobenzoxy, Ph is for phenyl, PMB is for p-methoxybenzyl, and POM is for pivaloyloxymethyl, respectively.

EXAMPLE 1

(Salt formation)

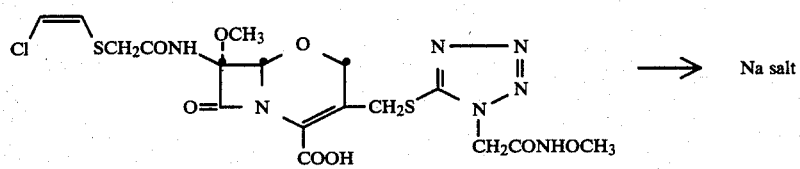

A solution of 7β-(2-(2-chlorovinyl(thioacetamido)-7α-methoxy-3-[1-(N-methoxycarbamoylmethyl)-1H-tetrazol-5-ylthiomethyl]-1-dethia-1-oxa-3-cephem-4-carboxylic acid in aqueous sodium hydrogen carbonate (10 parts) at pH of 5.2. The solution is concentrated in vacuum and lyophilized to give the corresponding sodium salt. Yield: 95%.

EXAMPLE 2

(Salt formation)

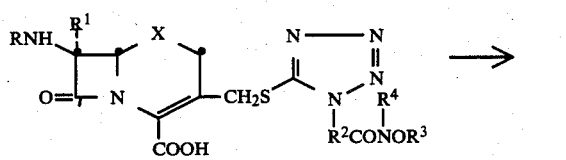

(1)

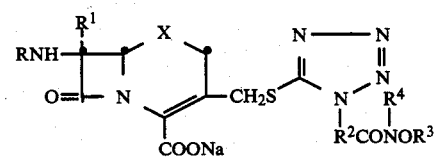

(2)

To a solution of Carboxylic acid (1) (1 g) in aqueous 0.5% sodium hydrogen carbonate (5 ml) adjusted to pH 7 with hydrochloric acid is washed with ethyl acetate, desalted, and poured into 10 ml vials. This is lyophilized conventionally to give the corresponding sodium salt (2) as powder.

The sodium salt produced under sterile condition (1 g) is dissolved in sterile water (4 g) is injected twice a day intravenously to a patient suffering from Staphylococcus aureus infection for treating said disease. This sodium salt (2) is assayed for MIC by the standard method of Japan Society of Chemotherapy to give values less than 0.1 g/ml against Streptococcus pyogenes C-203 and less than 0.1 g/ml against Escherichia coli JC-2.

EXAMPLE 3

(SHet introduction)

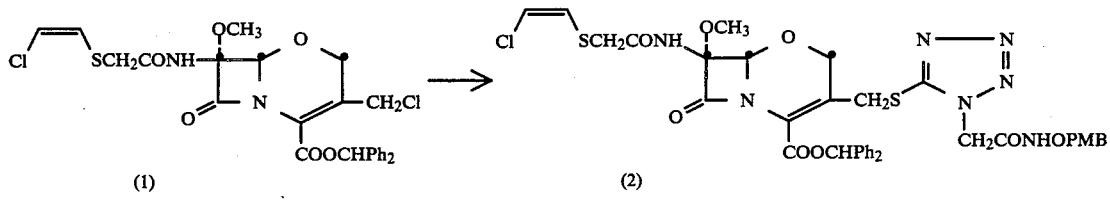

To a solution of 7β-(2-(2-chlorovinyl)thioacetamido)-7α-methoxy-3-chloromethyl-1-dethia-1-oxa-3-cephem-4-carboxylic acid diphenylmethyl ester in N,N-dimethylforamide (3 parts) is added a solution of mercaptide prepared from 1-(N-p-methoxybenzyloxycarbamoylmethyl)-1H-tetrazol-5-yl thiol (1.3 equivalents) and 4.5M sodium methoxide (1.35 equivalents) in N,N-dimethylformamide (4 parts). After 20 minutes, the reaction mixture is dissolved in ethyl acetate or dichloromethane and shaken with brine. The organic layer is washed with water, dried and concentrated in vacuo. The residue is chromatographed over silica gel to give 7β-(2-(2-chlorovinyl)thioacetamido)-7α-methoxy-3-[1-(N-p-methoxybenzyloxycarbamoylmethyl)-1H-tetrazol-5-ylthiomethyl]-1-diethia-1-oxa-3-cephem-4-carboxylic acid diphenylmethyl ester. Yield: 95%.

Similarly, 1-(N-p-methoxybenzyloxycarbamoylmethyl)-1H-tetrazol-5-ylthiol is replaced by other heterocyclic thiol to give the corresponding compounds listed in Table 1.

EXAMPLE 4

(SHet introduction)

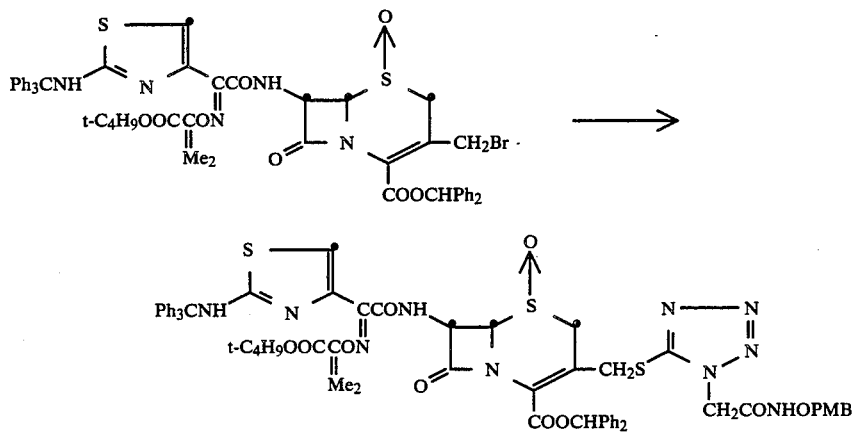

To a solution of 7β-[2-(2-triphenylmethylaminothiazol-4-yl)-2-t-butoxycarbonylisopropyloxyiminoacetamido]-3-bromomethyl-3-cephem-4-carboxylic acid diphenylmethyl ester 1-oxide in N,N-dimethylformamide (10 parts) is added a solution of 1-N-(p-methoxybenzyloxy)carbamoylmethyl-1H-tetrazol-5-ylthiol sodium salt (1 equivalent) in N,N-dimethylformamide with stirring. After 1 hour's stirring, the mixture is diluted with ethyl acetate, washed with water, dried and concentrated. The residue is 7β-[2-(2-triphenylmethylamino-4-thiazolyl)-2-(t-butoxycarbonylisopropoxyimino)acetamido]-3-[1-(N-p-methoxybenzyloxycarbamoyl)methyl-1H-tetrazol-5-yl]thiomethyl-3-cephem-4-carboxylic acid diphenylmethyl ester 1-oxide. Yield: 71%.

EXAMPLE 5

(Amidation)

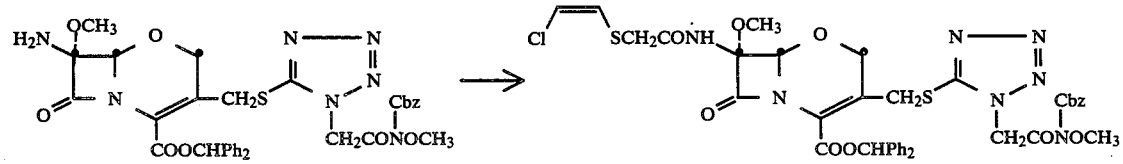

To a solution of 7β-amino-7α-methoxy-3-[1-(N-methoxy-N-carbobenzoxycarbamoyl)methyl-1H-tetrazol-5-ylthiomethyl]-1-dethia-1-oxa-3-cephem-4-carboxylic acid diphenylmethyl ester in dichloromethane (10 parts) cooled at −30° C. is added a solution of acid chloride prepared from 2-(2-chlorovinyl)thioacetic acid (1.4 equivalents), pyridine (5 equivalents), and phosphorus oxychloride (1.4 equivalents). After stirring for 30 minutes under ice cooling, the reaction mixture is washed with water, dried and concentrated to give 7β-[2-(2-chlorovinylthio)acetamido]-7α-methoxy-3-[1-(N-methoxy-N-carbobenzoxycarbamoylmethyl)-1H-tetrazol-5-yl]thiomethyl-1-dethia-1-oxa-3-cephem-4-carboxylic acid diphenylmethyl ester. Yield: 68.1%.

EXAMPLE 6

(Amidation)

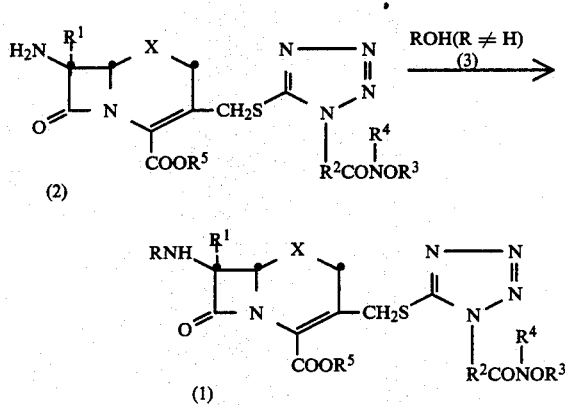

In a manner similar to Example 5, the corresponding 7β-amino compound (2) (1 equivalent) is treated with Carboxylic acid corresponding to the 7β-side chain (3) or its reactive derivative to give an amide (1), e.g., by a method as exemplified below:

(1) Amine (2) having COOR⁵ as carboxy is dissolved in aqueous (10 volumes) sodium hydrogen carbonate (2.5 equivalents). Carboxylic acid (3) chloride (1.1 equivalent) is dropwise added thereto. The mixture is kept at −5° C. to room temperature for 30 minutes to 2 hours.

(2) Amine (2) having COOR⁵ as carboxy is treated with trimethylsilyl chloride and triethylamine (1.2 equivalents each) to O-silylate, and then treated with pyridine (4 eqivalents) and Carboxylic acid (3) chloride (1.1 equivalents) at −30° C. for between 30 minutes and 2 hours, and then the obtained silyl ester is hydrolyzed with acid.

(3) In a solution of picoline (4 equivalents) and Carboxylic acid (3) chloride (1.2 equivalents) in dichloromethane (20 volumes) at 0° C. to −30° C. over 30 minutes and 2 hours.

(4) In a mixture of dimethylformamide (2 volumes) and ethyl acetate (10 volumes), treated with triethylamine (1.1 equivalent) and Carboxylic acid (3) chloride (1.1 equivalent) at 0° C. to −20° C. for between 30 minutes and 3 hours.

(5) In a mixture of chloroform (10 volumes) and dimethoxyethane (10 volumes), pyridine (1.5 moles), and a mixed anhydride of Carboxylic acid (3) and isobutoxyformic acid, stirred at a temperature between −5° to 10° C. over a 30 minutes and 6 hour period.

(6) In a mixture of ethyl acetate (10 volumes), 1,2-dichloroethane (10 volumes), 4-methylmorpholine (1.5 equivalents), and the symmetric anhydride of Carboxylic acid (3) (1.1 equivalent), refluxed for 10 minutes to 2 hours.

(7) In a mixture of dichloromethane (10 volumes), pyridine (1.5 equivalents), and mixed anhydride of Carboxylic acid (3) and methanesulfonic acid (1.1 equivalent), kept at between 0° C. to room temperature over 1 to 3 hours.

(8) In a mixture of dimethylformamide (5 volumes), dimethylaniline (1.3 equivalents) and the Vilsmeyer reagent made from Carboxylic acid (3) and dimethylformamide (1.1 equivalent), stirred at room temperature for 1 to 5 hours.

(9) In a mixture of ethyl acetate (10 volumes), pyridine (1.5 equivalents) and a mixed anhydride of diethyl hydrogen phosphate and Carboxylic acid (3) (1.5 equivalents), stirred at 0° C. to 10° C. for 1 to 5 hours.

(10) In a mixture of ethyl acetate (7 volumes), dichloromethane (10 volumes), pyridine (1 equivalent), and the mixed anhydride of Carboxylic acid (3) and dichlorophosphoric acid (1.1 equivalent), stirred for 1 to 3 hours at 0° C. to room temperature.

(11) In a mixture of lutidine (1.5 equivalents), dichloromethane (10 volumes), and the mixed anhydride (1.1 to 2 equivalents) of Carboxylic acid (3) and monochlorophosphoric acid dimethylamide, stirred for 1 to 4 hours at 0° to 30° C.

(12) In a mixture of carbonyldiimidazole (1.1 equivalent), tetrahydrofuran (10 volumes), dimethylacetamide (5 volumes), and Carboxylic acid (3) (1.1 equivalent), stirred for 1 to 5 hours at 0° C. to room temperature.

(13) In a mixture of dichloromethane (10 volumes), dimethylformamide (5 volumes), N,N-dicyclohexylcarbodiimide (1.1 equivalent), picoline (1.2 equivalents), and Carboxylic acid (3) (1.1 equivalent), stirred at 0° to 40° C. for 2 hours to 24 hours.

(14) In a mixture of dichloromethane (10 volumes), 2-ethoxy-1-ethoxycarbonyl-1,2-dihydroquinoline (1.1 equivalent), N,N'-dicyclohexylcarbodiimide (1.1 equivalent), pyridine (1.5 equivalents), and Carboxylic acid (3) (1.1 equivalent), stirred for 1 to 6 hours at 0° C. to room temperature to 2 hours at −30° C. to 0° C.

(15) In a mixture of dichloromethane (30 volumes), cyanuric chloride (1.1 equivalent), pyridine (4 equivalents), and Carboxylic acid (3) (1.1 equivalent), stirred for 30 minutes

(16) In a mixture of dichloromethane (3 volumes), phosphorus oxychloride (1.1 equivalent), pyridine (1.5 equivalents), and Carboxylic acid (3) (1.1 equivalent), stirred for 20 minutes to 2 hours at −10° C. to 10° C.

(17) Amine (2) is treated with trimethylsilyl chloride to obtain the corresponding N-trimethylsilyl compound, and this is treated with phosphorus oxychloride (1.5 equivalents), Carboxylic acid (3) (1.2 equivalents), and pyridine (4 equivalents) in dichloromethane (5 parts) for 30 minutes to 2 hours at 0° C. to room temperature.

(18) In a mixture of dichloromethane (8 volumes), thionyl chloride (1.5 equivalents), pyridine (2.5 equivalents), and Carboxylic acid (3) (1.1 equivalent), stirred for 1 to 5 hours at −30° to 0° C.

(19) In a mixture of dichloromethane (20 volumes), 1-hydroxybenzotriazole (2.1 equivalent), N,N'-dicyclohexylcarbodiimide (2.5 equivalents) and Carboxylic acid (3) (2 equivalents), stirred at room temperature for 1 to 15 hours.

(20) In a mixture of dichloromethane (5 volumes), trifluoroacetic anhydride (1.5 equivalents), pyridine (3 equivalents), and Carboxylic acid (3) (1.5 equivalents), stirred for 1 to 5 hours at 0° C. to room temperature.

(21) In a mixture of dichloromethane (10 volumes), bromide of diethyl hydrogen phosphate (1.2 equivalents), 4-methylmorpholine (2.5 equivalents), and Carboxylic acid (3) (1.2 equivalents), stirred for 1 to 3 hours at 0° C. to room temperature.

(22) In a mixture of ethyl acetate (10 volumes), di-2-pyridyl disulfide (1.1 equivalent), triphenylphosphine (1.1 equivalent), and Carboxylic acid (3) (1.1 equivalent), stirred for 2 to 6 hours at 10° to 50° C.

(23) In a mixture of dichloromethane (3 volumes), 1,3,5-tripyridiniumtriazine trichloride (4 equivalents), and Carboxylic acid (3) (1.1 equivalent), stirred for 1 to 5 hours at −10° to 10° C.

(24) In a mixture of carbon tetrachloride (30 volumes), 4-methylmorpholine (1.5 equivalents), trisdiethylaminophosphine (1.1 equivalent) and Carboxylic acid (3) (1.1 equivalent), kept for 1 to 5 hours at −20° to 10° C.

(25) In a mixture of dioxane (10 volumes) and phthalimide of Carboxylic acid (3) (2 equivalents), stirred for 2 to 8 hours at 10° to 50° C.

(26) In a mixture of methyl isobutyl ketone (10 volumes) and succinimide of Carboxylic acid (3) (1.5 equivalents), stirred for 2 to 9 hours at 0° to 40° C.

(27) In a mixture of dichloromethane (20 volumes), pyridine (3 equivalents), and 1-oxybenzotriazolyl ester of Carboxylic acid (3) (3 equivalents), stirred for 5 to 30 hours at 10° to 50° C.

(28) In a mixture of chloroform (3 volumes), toluene (1 volume), picoline (2 equivalents), oxalyl chloride (1 equivalent) and Carboxylic acid (3) (1.1 equivalent), stirred for 10 minutes to 2 hours at −50° C. to 10° C.

In above examples, volume is expressed by ml per gram of the starting Amine (2) and equivalent shows molar equivalent per 1 molar equivalent of the starting Amine (2).

To a solution of 7β-benzoylamino-3-[1-(N-methoxy-N-carbobenzoxycarbamoylmethyl)-1H-tetrazol-5-ylthiomethyl]-7α-methoxy 1-dethia-1-oxa-3-cephem-4-carboxylic acid diphenylmethyl ester in dichloromethane (5 volumes) under ice cooling are added pyridine (1.8 equivalents) and phosphorus oxychloride or pentachloride (1.6 equivalents). After 2 hour's stirring at room temperature, the reaction mixture containing 7β-(α-chlorobenzylideneamino)-7α-methoxy-3-[1-(N-methoxy-N-carbobenzoxycarbamoylmethyl)-1H-tetrazol-5-ylthiomethyl]-1-dethia-1-oxa-3-cephem-4-carboxylic acid diphenylmethyl ester is cooled to −20° C., diluted with methanol (3 ml) and stirred for 2 hours under ice cooling. To the solution containing 7β-(α-methoxybenzylideneamino)-7α-methoxy-3-[1-(N-methoxy-N-carbobenzoxycarbamoylmethyl)-1H-tetrazol-5-ylthiomethyl]-1-dethia-1-oxa-3-cephem-4-carboxylic acid diphenylmethyl ester cooled at −30° C. is added pyridine (1 part). After stirring for 20 minutes at −30° C., the solution is diluted with dichloromethane and 2N-phosphoric acid, stirred and shaken. The organic layer is collected, washed with water, dried, and concentrated in vacuum. The residue is purified by silica gel chromatography to give 7β-amino-7α-methoxy 3-[1-(N-methoxy-N-carbobenzoxycarbamoylmethyl)-1H-tetrazol-5-yl-thiomethyl]-1-dethia-1-oxa-3-cephem-4-carboxylic acid diphenylmethyl ester. Yield: 45.5%.

Similarly prepared are 7β-amino compounds having 1-thia-nucleus, 1-oxa nucleus, or various tetrazolyl groups.

EXAMPLE 8
(COOH deprotection)

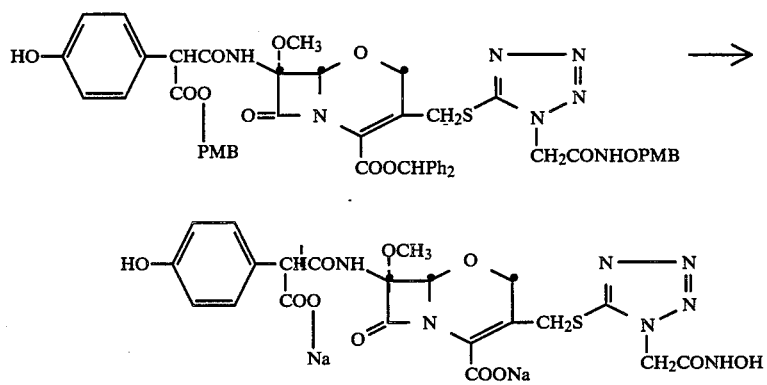

EXAMPLE 7
(Deacylation)

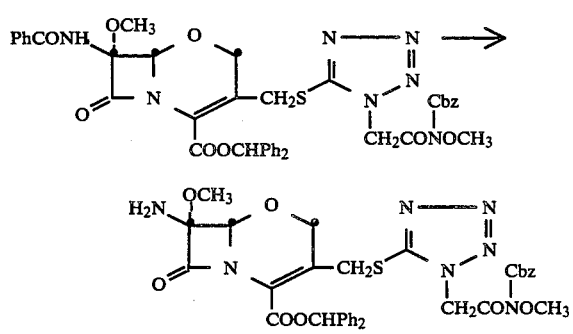

To a solution of 7β-(2-p-hydroxyphenyl-2-p-methoxybenzyl-oxycarbonylacetamido)-7α-methoxy-3-(1-(N-p-methoxybenzyloxycarbamoylmethyl)-1H-tetrazol-5-ylthiomethyl]-1-dethia-1-oxa-3-cephem-4-carboxylic acid diphenylmethyl ester in dichloromethane (10 parts) cooled at −10° C. is added a solution of anisole (5 equivalents), aluminum chloride (3 equivalents), and nitromethane (4 parts) and the mixture is stirred at −10° C. for 1 hour. The reaction mixture is concentrated. The residue is poured into 2% hydrochloric acid and extracted with methyl ethyl ketone. The extract is washed with water, dried and concentrated to give 7β-(2-p-hydroxyphenyl-2-carboxyacetamido)-7α-methoxy-3-[1-(N-hydroxycarbamoylmethyl)-1H-tetrazol-5-ylthiomethyl] -1-dethia-1-oxa-3-cephem-4-carboxylic acid. Yield: 85%. The product is dissolved in 2% sodium hydrogen carbonate, made pH 6.5, and lyophilized in a usual manner to give the corresponding disodium salt in 80% yield.

The same product is produced from 7β-[2-p-(p-methoxybenzyloxy)phenyl-2-p-methoxybenzyloxycarbonylacetamido]-7α-methoxy-3-[1-(N-p-methoxybenzyloxycarbamoylmethyl)-1H-tetrazol-5-ylthiomethyl]-1-dethia-1-oxa-3-cephem-4-carboxylic acid p-methoxybenzyl ester under the same reaction condition.

EXAMPLE 9

(Deprotection)

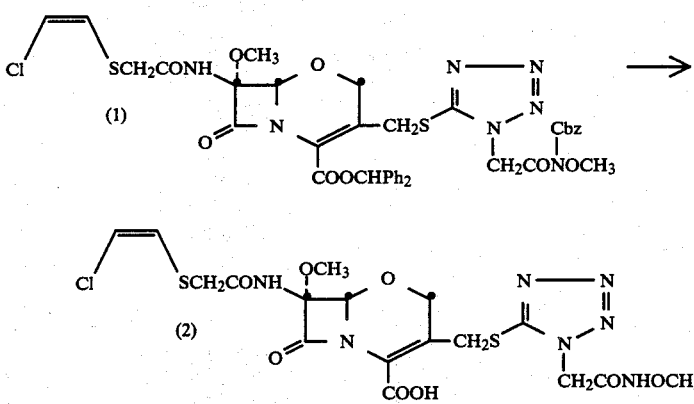

To a solution of 7β-(2-(2-chlorovinyl)thioacetamido)-7α-methoxy-3-[1-(N-methoxy-N-carbobenzoxycarbamoylmethyl)-1H-tetrazol-5-ylthiomethyl]-1-cethia-1-oxa-3-cephem-4-carboxylic acid diphenylmethyl ester in dichloromethane (10 parts) cooled at −20° C. is added a solution of aluminum chloride (10 equivalents) in anisole (10 parts). After stirring for 15 minutes under ice cooling, the reaction mixture is diluted with ether and aqueous 5% sodium hydrogen carbonate and filtered. The water layer is washed with ether, acidified with hydrochloric acid, and extracted with methyl ethyl ketone under salt out condition. The extract is dried, concentrated in vacuum, and the residue washed with ether. The resulting crystals are collected to give 7β-(2-(2-chlorovinyl)thioacetamido)-7α-methoxy-3-[1-(N-methoxycarbamoylmethyl)-1H-tetrazol-5-ylthiomethyl]-1-dethia-1-oxa-3-cephem-4-carboxylic acid in 85.1% yield.

Similarly prepared are free acids from the corresponding diphenylmethyl esters of Table 1.

When the starting compound has diphenylmethyl ester, p-methoxybenzyl ester, t-butyl ester, t-butoxyformamide, benzyloxyformamide, etc., deprotected under above condition gives the corresponding carboxylic acid, amine, etc.

EXAMPLE 10

(Deesterification)

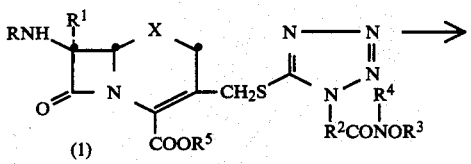

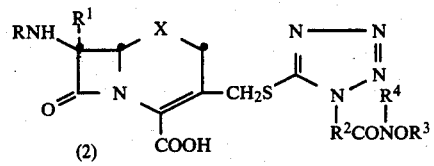

(1) A solution of the p-methoxybenzyl ester or diphenylmethyl ester (1) (1 part) in a mixture of dichloromethane (0.3 to 3 parts), trifluoroacetic acid (0.3 to 3 parts) and anisole (0.5 to 5 parts) is stirred at −10° to 40° C. for 10 minutes to 3 hours. The reaction mixture is concentrated in vacuum to remove the solvent and reagent. The residue is washed with benzene to give the corresponding free acid (2). Yield: 70 to 90%

(2) To a solution of above starting material (1) (1 part) in a mixture of dichloromethane (5 to 9 parts) and anisole (2 to 8 parts) is added aluminum chloride (2 to 4 equivalents) and stirred for 1 to 3 hours at −10° to 10° C. The reaction mixture is washed with diluted hydrochloric acid and water, dried and concentrated to give the corresponding free acid (2). Yield: 80 to 95%.

EXAMPLE 11

(Modification)

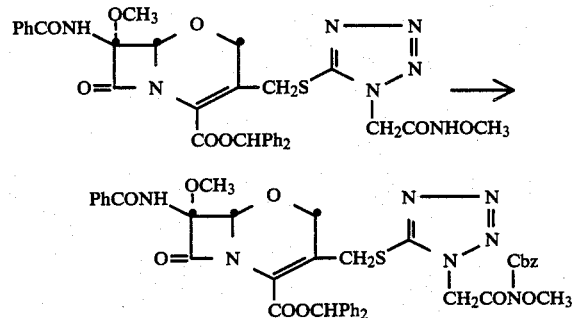

To a solution of 7β-benzamido-7α-methoxy-3-[1-(N-methoxycarbamoylmethyl)-1H-tetrazol-5-ylthiomethyl]-1-dethia-1-oxa-3-cephem-4-carboxylic acid diphenylmethyl ester in dichloromethane (6 parts) are added N-methylmorpholine (1.4 equivalents) and benzyl chloroformate (1.2 equivalents) at −10° C. After stirring at 0° C. for 20 minutes, the reaction mixture is diluted with dichloromethane, washed with water, dried and concentrated in vacuum to give 7β-benzamido-7α- methoxy-3-[1-(N-methoxy-N-carbobenzoxycarbamoyl-methyl)-1H-tetrazol-5-yl-thiomethyl]-1-dethia-1-oxa-3-cephem-4-carboxylic acid diphenylmethyl ester. Yield: 90.3%.

EXAMPLE 12

(Modification)

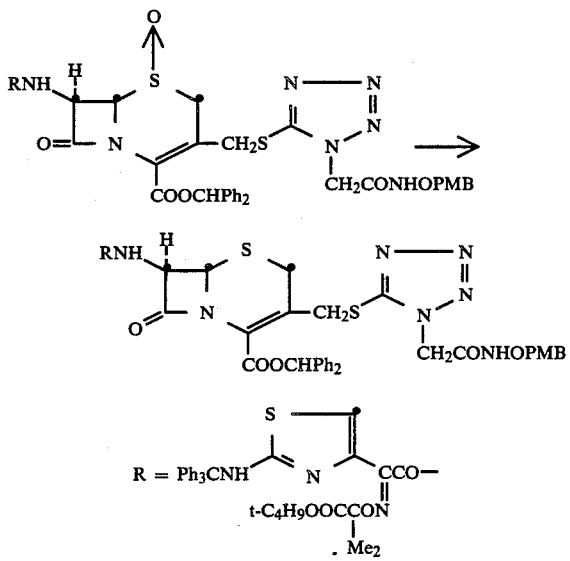

To a solution of 7β-[2-(2-triphenylmethylamino-4-thiazol-yl)-2-(t-butoxycarbonylisopropox-yimino)acetamido]-3-[1-(N-p-methoxybenzyloxycar-bamoylmethyl)-1H-tetrazol-5-ylthiometyl]-3-cephem-4-carboxylic acid diphenylmethyl ester 1-oxide and potassium iodide (2 parts) in acetone (20 parts) cooled at −15° C. is added with acetyl chloride (5 equivalents). After 40 minutes stirring at −15° C., the reaction mixture is diluted with saturated brine, water, and sodium hydrogen carbonate and extracted with dichloromethane. The extract is washed with water, dried, and concentrated to afford the corresponding sulfide. Yield: 73%.

By oxidizing this product with m-chloroperbenzoic acid (1 equivalent) for 5 hours at room temperature, one obtains the starting 1-oxide given above in 75% yield.

EXAMPLE 13

(Deprotection)

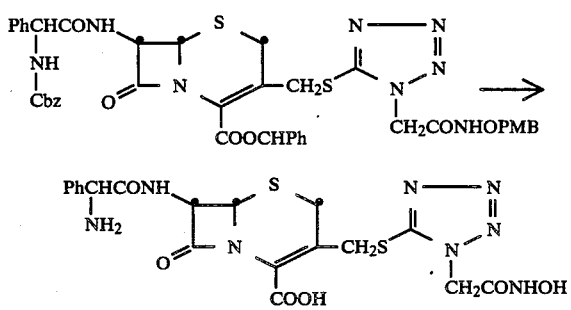

To a solution of 7β-(2-phenyl-2-carbobenzox-yaminoacetamido)-3-[1-(N-p-methoxybenzyloxycar-bamoylmethyl)-1H-tetrazol-5-ylthiomethyl]-3-cephem-4-carboxylic acid diphenylmethyl ester in dichloromethane (10 parts) are added aluminum chloride (3 equivalents) and anisole (5 equivalents) at −10° C., and the mixture is stirred at −10° C. for 1 hour. The mixture is poured into cold hydrochloric acid and washed with ethyl acetate. The aqueous layer is separated, absorbed on a column filled with styrene-divinylbenzene copolymer, and eluted with aqueous 10 to 20% acetone. The eluate is lyophillized in a conventional manner to give the 7β-phenylglycinamido-3-[1-(N-hydroxycar-bamoylmethyl)-1H-tetrazol-5-ylthio]methyl-3-cephem-4-carboxylic acid. Yield: 40%.

EXAMPLE 14

(Deprotection)

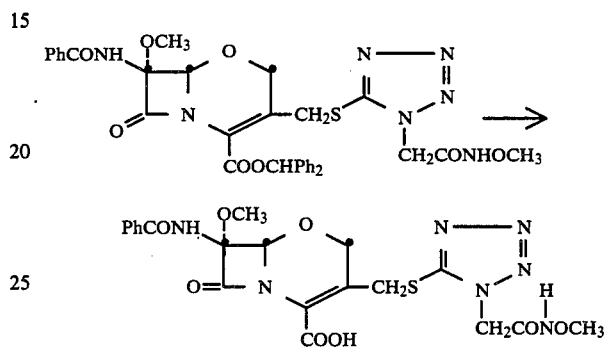

To a solution of 7β-benzamido-7α-methoxy-3-[1-(N-methoxycarbamoylmethyl)-1H-tetrazol-5-ylthiome-thyl]-1-dethia-1-oxa-3-cephem-4-carboxylic acid diphenylmethyl ester in dichloromethane (10 parts) is added a solution of anisole (5 equivalents) and aluminum chloride (3 equivalents) in nitromethane (50 parts) at −20° C. After stirring at −20° C. for 30 minutes, the mixture is poured into ice water containing diluted hydrohydrochloric acid and extracted with methyl ethyl ketone and ethyl acetate. The extract is washed with water and reextracted into diluted aqueous sodium hydrogen carbonate. The aqueous extract is acidified with hydrochloric acid and extracted with methyl ethyl ketone and ethyl acetate. The extract is washed with water, dried, and concentrated to give the corresponding free acid in 89.2% yield.

EXAMPLE 15

(Methoxylation)

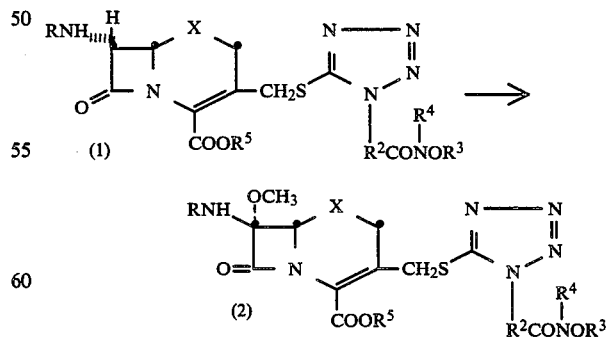

To a solution of 7α-amido-3-substituted methyl-1-dethia-1-oxa-3-cephem-4-carboxylic acid derivative (1) (1 part) in dichloromethane (10 parts) is added tert-butyl hypochlorite (1.1 equivalent). After standing for 3 hours at −20° C., a solution of lithium methoxide (1.2 equivalents) in methanol is added to the mixture and let react for 30 minutes. The reaction mixture is acidified with acetic acid and diluted with dichloromethane. This is washed with water, dried, and concentrated in vacuum to give the corresponding 7β-amido-7α-methoxy-3-substituted methyl-1-dethia-1-oxa-3-cephem-4-carboxylic acid derivative (2) in 40 to 85% yield.

EXAMPLE 16

(Pharmacologically acceptable esters)

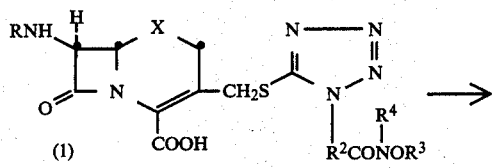

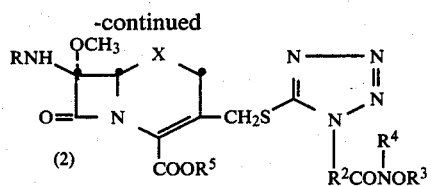

(1) To a solution of Carboxylic acid (1) potassium salt (1 millimole) in N,N-dimethylformamide (2 to 5 parts) is added iodomethyl pivalate (1 to 2 equivalents) under ice cooling. After 15 minutes to 2 hours' stirring, the mixture is diluted with ethyl acetate, washed with ice water and aqueous sodium hydrogen carbonate, dried, and concentrated in vacuum. The residue is recrystallized from ethyl acetate to give the pivaloyloxymethyl ester (2) of the carboxylic acid.

(2) The potassium salt of above section (1) is replaced by sodium salt to give the same products under same condition.

(3) Pivaloyloxymethyl ester (2) of above section (1) (250 mg), corn starch (150 mg), and magnesium stearate (5 mg) are mixed, granulated, and encapsulated in a conventional manner.

This capsule (1 to 3 capsules) are given orally to treat a patient suffering from infection caused by sensitive Staphylococcus aureus.

(4) In place of iodomethyl pivalate of above (1), iodomethyl acetate of iodoethyl ethoxyformate is used under the same condition to give the corresponding acetoxymethyl ester (2) or ethoxycarbonyloxyethyl ester (2).

TABLE 1

$$\text{RNH-}\overset{R^1}{\underset{}{\text{C}}}\text{-[structure with X, N, CH}_2\text{S, COOR}^5\text{, and side chain OR}^3\text{/R}^4\text{]}$$

| No. | R | $R^1$ | X | $R^3$ | $R^4$ | $R^5$ | IR | NMR |
|---|---|---|---|---|---|---|---|---|
| 1 | H | CH$_3$O | O | CH$_3$ | Cbz | BH | CHCl$_3$: 3330,1781, 1721,1603, 1499. | CDCl$_3$: 2.14(s, 2H), 3.48(s, 3H), 3.76 (s, 3H), 4.22(s, 2H), 4.52d + 4.65d (ABq, 2H, J=18), 4.83(s, 1H), 4.98 (s, 2H), 5.13(s, 2H), 6.93(s, 2H). |
| 2 | NCCHCO—<br>$\|$<br>C$_2$H$_5$ | CH$_3$O | O | O | (3-CH$_2$Cl)*$^1$ | BH | CHCl$_3$: 3300,2240, 1792,1718, 1498. | CDCl$_3$: [1.07(t, J=7) + 1.10(t, J=7)] 3H, [2.98(dq, J=7; 7) + 3.00(dq, J=7; 7)]2H, 3.48(t, 1H, J=7), 3.56(s, 3 H), 4.47(s, 2H), 4.52(s, 2H), 5.07 (s, 1H), 6.96(s, 1H), 7.20–7.80(m, 10 H). |
| 3 | NCCHCO—<br>$\|$<br>C$_2$H$_5$ | CH$_3$O | O | H | H | POM | KBr: 3300,2240, 1787,1750, 1690,1630, 1525. | CD$_3$COCD$_3$: 1.08(t, 3H, J=7), 1.22(s, 9H), 2.02(dq, 2H, J=7; 7), 3.50(s, 3 H), 3.82(t, 1H, J=7), 4.20(d, 1H, J= 13), 4.50(d, 1H, J=13), 4.66(s, 2H), 5.13(s, 3H), 5.86(d, 1H, J=6), 6.05 (d, 1H, J=6). |
| 4 | NCCHCO—<br>$\|$<br>C$_2$H$_5$ | CH$_3$O | O | CH$_3$ | H | BH | CHCl$_3$: 3400,2240, 1793,1725, 1497. | CDCl$_3$: 1.04(t, 3H, J=7), 1.93(dq, 2H, J=7; 7), 3.5(brs, 1H), 3.53(s, 3H), 3.65(s, 3H), 4.15(s, 2H), 4.51(s, 2H), 4.85(brs, 2H), 5.04(s, 1H), 6.88(s, 1H), 7.20–7.70(m, 10H). |
| 5 | NCCHCO—<br>$\|$<br>C$_2$H$_5$ | CH$_3$O | O | H | H | Na | KBr: 3500–3200, 2240,1770, 1691,1608, 1525. | D$_2$O: 1.06(t, 3H, J=7), 1.97(dq, 2H, J=7; 7), 3.5(brs, 1H), 3.54(s, 3H), 4.13(d, 1H, J=13), 4.30(d, 1H, J=13), 4.53(s, 2H), (5.17 + 5.21s)3H. |
| 6 | NCCHCO—<br>$\|$<br>C$_2$H$_5$ | CH$_3$O | O | CH$_3$ | H | Na | CHCl$_3$: 3300,2240, 1793,1715, 1615,1514, 1500. | CDCl$_3$: 1.03(t, 3H, J=7), 1.90(dq, 2H, J=7; 7), 3.44(t, 1H, J=7), 3.52(s, 3H), 3.73(s, 3H), 3.94(s, 2H), 3.99 (s, 2H), 4.73(s, 4H), 5.02(s, 1H), 6.87(s, 1H), 6.84(d, 2H, J=7), 7.10–7.70(m, 13H). |

TABLE 1-continued

![structure: RNH-R¹ on β-lactam with X, N, COOR⁵, CH₂S, substituted triazole with OR³ and CH₂CON-R⁴]

| No. | R | R¹ | X | R³ | R⁴ | R⁵ | IR | NMR |
|---|---|---|---|---|---|---|---|---|
| 7 | NCCHCO—<br>　│<br>　C₂H₅ | CH₃O | O | CH₃ | H | Na | KBr: 3500–3200, 2245,1768, 1695,1608, 1525. | D₂O: 1.08(t, 3H, J=7), 1.98dq, 2H, J=7; 7), 3.56(s, 3H), 3.79(s, 3H), 3.81 (brs, 1H), 4.19(d, 1H, J=13), 4.33(d, 1H, J=13), 4.54(s, 2H), (5.18s + 5.20s)3H. |
| 8 | NCCHCO—<br>　│<br>　C₂H₅ | CH₃O | O | CH₃ | H | BH | CHCl₃: 3280,1787, 1720,1610. | CDCl₃: 3.47(s, 3H), 3.58(s, 3H), 3.70 (s, 3H), 3.93–5.17(m, 8H), 6.47–7.67 (m, 20H). |
| 9 | HO—⟨⟩—CHCO—<br>　　　　　│<br>　　　　COOPMB | CH₃O | O | PMB | H | BH | CHCl₃: 3300,1785, 1720,1610. | CDCl₃: 3.45(s, 3H), 3.67(s, 3H), 3.68 (s, 3H), 3.88–5.12(m, 12H), 6.47–7.62(m, 24H). |
| 10 | HO—⟨⟩—CHCO—<br>　　　　　│<br>　　　　COONa | CH₃O | O | H | H | Na |  | D₂O: (3.88s + 3.95s)3H, 4.53–4.73(m, 2H), 4.82–4.95(m, 3H), 5.58(brs, 3H), 7.30(d, 2H, J=9), 7.72(d, 2H, J=9) |
| 11 | HO—⟨⟩—CHCO—<br>　　　　　│<br>　　　　COONa | CH₃O | O | CH₃ | H | Na |  | D₂O: (3.92s + 3.98s)3H, 4.20(s, 3H), 4.60–4.80(m, 2H), 4.92(brs, 3H), 5.50–5.67(m, 3H), 7.33(d, 2H, J=9), 7.75(d, 2H, J=9). |
| 12 | HO—⟨⟩(F)—CHCO—<br>　　　　　│<br>　　　　COOH | CH₃O | O | H | H | H | Nujol: 3200,1775, 1680,1625. | CDCl₃ + CD₃OD(2:1): (3.48s + 3.54s)3H, 4.25(brs, 2H), 4.53 (brs, 2H), 6.40–7.45(m, 3H). |
| 13 | HO—⟨⟩(F)—CHCO—<br>　　　　　│<br>　　　　COOH | CH₃O | O | CH₃ | H | H | Nujol: 3180,1780, 1690,1625. | CDCl₃ + CD₃OD(3:1): (3.47s + 3.51s)3H, 3.71(s, 3H), 4.24 (brs, 2H), 4.53(brs, 2H), 4.87(s, 1H), 4.97(brs, 2H), 5.06(s, 1H), 6.40–7.43(m, 3H). |

TABLE 1-continued

Structure:
RNH-[R¹]-[β-lactam with X]-CH₂S-C(=N-N=)-N(OR³)(R⁴)-CH₂CON, COOR⁵

| No. | R | R¹ | X | R³ | R⁴ | R⁵ | IR | NMR |
|---|---|---|---|---|---|---|---|---|
| 14 | 2-F, 4-PMBO-phenyl-CHCO-COOPMB | CH₃O | O | CH₃ | H | BH | CHCl₃: 3250, 1790, 1720, 1615. | CDCl₃: (3.45s + 3.47s)3H, 3.58(s, 3H), 3.73 (s, 3H), 3.77(s, 3H), 4.12(brs, 2H), 4.41(brs, 2H), 4.70(brs, 2H), 4.84 (s, 1H), 4.90(s, 2H), 5.00(s, 1H), 5.09(s, 2H), 6.86(s, 1H), 6.60–7.63 (m, 21H). |
| 15 | 2-F, 4-PMBO-phenyl-CHCO-COOPMB | CH₃O | O | CH₃ | H | BH | CHCl₃: 3300, 1790, 1720, 1615. | CDCl₃: 3.47(brs, 3H), 3.70(s, 3H), 3.73(s, 3H), 3.77(s, 3H), 4.11(brs, 2H), 4.40(brs, 2H), 4.69(brs, 2H + 2H), 4.80(s, 1H), 4.89(s, 2H), 4.99(s, 1H), 5.09(s, 2H), 6.86(s, 1H), 6.50–7.63(m, 25H). |
| 16 | thienyl-CHCO-COOBH | CH₃O | O | (3-CH₂Cl)*¹ | | BH | CHCl₃: 3400, 3370, 1792, 1728, 1700, 1497. | CDCl₃: (3.36s + 3.39s)3H, 4.33(s, 2H), 4.35(d, 1H, J=11), 4.48(d, 1H, J=11), 4.85(s, 1H), (4.97s + 5.00s)1H, 6.92(s, 2H), 7.00–7.70(m, 24H). |
| 17 | thienyl-CHCO-COOBH | CH₃O | O | CH₃ | H | BH | CHCl₃: 3300, 1793, 1720, 1497. | CDCl₃: 3.39(s, 3H), 3.56(s, 3H), 4.10 (s, 2H), 4.37(s, 2H), 4.67(brs, 2H), 4.87(s, 1H), (4.96s + 4.98s)1H, 6.88(s, 2H), 7.00–7.80(m, 24H). |
| 18 | thienyl-CHCO-COOBH | CH₃O | O | PMB | H | BH | CHCl₃: 3350, 1790, 1720, 1615, 1515, 1497. | CDCl₃: 3.36(s, 3H), 3.67(s, 3H), 4.10 (s, 2H), 4.35(s, 2H), 4.67(s, 4H), 4.83(s, 1H), (4.94s + 4.96s)1H, 6.86(s, 2H), 6.83(d, 2H, J=11), 6.95–7.80 (m, 25H). |
| 19 | thienyl-CHCO-COONa | CH₃O | O | H | H | Na | KBr: 3400, 1768, 1680, 1603, 1510. | D₂O: (3.47s + 3.52s)3H, 4.11(d, 1H, J=13), 4.30(d, 1H, J=13), 4.48(s, 2H), 4.97(s, 1H), 5.14(s, 3H), 7.15(d, 1H, J=5), 7.35–7.55(m, 2H). |

TABLE 1-continued

| No. | R | R¹ | X | R³ | R⁴ | R⁵ | IR | NMR |
|---|---|---|---|---|---|---|---|---|
| 20 | ![thiophene-CHCO-COONa] | CH₃O | O | CH₃ | H | Na | KBr: 3400,1767, 1685,1605, 1510. | D₂O: (3.48s + 3.54s)3H, 3.78(s, 3H), 4.13(d, 1H, J=13), 4.30(d, 1H, J=13), 4.48(s, 2H), 4.97(s, 1H), 5.16(s, 1H), 5.19(s, 2H), 7.16(d, 1H, J=5), 7.35–7.55(m, 2H). |
| 21 | phenyl-CO— | CH₃O | O | CH₃ | H | H | KBr: 1785,1705. | d₆-DMSO: 2.35(s, 3H), 3.43(s, 3H), [4.08d + 4.38d(ABq, 2H, J=14)], 7.25(d, 2H, J=8), 7.83(d, 2H, J=8). |
| 22 | phenyl-CO— | CH₃O | O | CH₃ | H | H | CHCl₃: 1685,1718. 1785. | CDCl₃: 2.37(s, 3H), 3.62(s, 3H), 4.20 (s, 2H), 4.55(s, 2H), 4.88(s, 2H), 5.17(s, 1H), 6.92(s, 1H), 7.03–8.00(m, 16H). |
| 23 | phenyl(BH)-CO— | CH₃O | O | CH₃ | Cbz | BH | CHCl₃: 3340,1783, 1721,1685, 1615. | CDCl₃: 2.32(s, 3H), 3.55(s, 3H), 3.68(s, 3H), 4.21(s, 2H), 4.52(s, 2H), 4.93(s, 2H), 5.06(s, 2H), 5.13(s, 1H), 6.91 (s, 1H). |
| 24 | C₂H₅N-...NCONHCHCO—C₂H₅ | CH₃O | O | H | H | H | KBr: 3300,1776, 1707,1670, 1517. dp. 187–9 C. | d₆-DMSO: 0.84(t, 3H, J=7), 1.07(t, 3H, J=7), 1.70(dq, 2H, J=7; 7), 3.40(q, 2H, J=7), 3.37(s, 3H), 3.5–3.7(m, 2H), 3.7–4.1(m, 2H), 4.15(d, 1H, J=15), 4.37(d, 1H, J=15), 4.50(brs, 1H), 4.51(s, 2H), (4.99s + 5.06s)3H, 9.23(d, 1H, J=7), 9.24(s, 1H). |
| 25 | C₂H₅N-...NCONHCHCO—C₂H₅ | CH₃O | O | CH₃ | H | H | KBr: 3300,1773, 1716,1663, 1516. | d₆-DMSO: 0.85(t, 3H, J=7), 1.08(t, 3H, J=7), 1.72(dq, 2H, J=7; 7), 3.38(s, 3H), 3.42(q, 2H, J=7), 3.5–3.8(m, 2H), 3.66(s, 3H), 3.8–4.1(m, 2H), 4.17(d, 1H, J=14), 4.37(d, 1H, J=14), 4.50(s, 2H), 4.50(brs, 1H)5.06(s, 3H), 9.23(d, 1H, J=7), 9.26(s, 1H). |

TABLE 1-continued

Structure:

$$\text{RNH}-\overset{R^1}{\underset{O}{\square}}-N-\overset{X}{\underset{COOR^5}{=}}-CH_2S-\underset{CH_2CON}{\overset{N=N}{\underset{\square}{N}}}\overset{OR^3}{\underset{R^4}{\square}}$$

| No. | R | $R^1$ | X | $R^3$ | $R^4$ | $R^5$ | IR | NMR |
|---|---|---|---|---|---|---|---|---|
| 26 | $C_2H_5N$—[ring]—NCONHCHCO—$C_2H_5$ (with diketone) | $CH_3O$ | O | $CH_3$ | H | BH | $CHCl_3$: 3280, 1790, 1715, 1687, 1528. | $CD_3COCD_3$: 0.94(t, 3H, J=7), 1.12(t, 3H, J=7), 1.86(dq, 2H, J=7; 7), 3.44(q, 2H, J=7), 3.54(s, 3H), 3.5-3.7(m, 2H), 3.70(s, 3H), 4.1-4.3(m, 2H), 4.27(s, 3H), 4.56(s, 2H), 4.62(t, 1H, J=7), 5.10(s, 3H), 6.93(s, 1H), 7.2-7.8 (m, 10H), 8.34(s, 1H), 9.39(d, 1H, J=7). |
| 27 | $C_2H_5N$—[ring]—NCONHCHCO—$C_2H_5$ | $CH_3O$ | O | PMB | H | BH | $CHCl_3$: 3280, 1790, 1715, 1690, 1614, 1514. | $CD_3COCD_3$: 0.94(t, 3H, J=7), 1.11(t, 3H, J=7), 1.87(dd, 2H, J=7; 7), 3.42(q, 2H, J=7), 3.53(s, 3H), 3.5-3.7(m, 2H), 3.74 (s, 3H), 3.9-4.2(m, 2H), 4.27(s, 2H), 4.57(s, 2H), 4.60(brs, 1H), 4.84(s, 2H), 5.11(s, 3H), 6.89(d, 2H, J=9), 6.93(s, 1H), 7.1-7.8(m, 12H), 8.36(s, 1H), 9.38(d, 1H, J=7). |
| 28 | $C_2H_5N$—[ring]—NCONHCHCO—$C_2H_5$ | $CH_3O$ | O | H | H | Na | KBr: 3500-3300, 1770, 1710, 1675, 1605, 1518. | $D_2O$: 0.98(t, 3H, J=7), 1.18(t, 3H, J=7), 1.88(dq, 2H, J=7; 7), 3.52(q, 2H, J=7), 3.53(s, 3H), 3.6-3.8(m, 2H), 3.9-4.1(m, 2H), 4.13(d, 1H, J=10), 4.29(d, 1H, J=10), 4.39(t, 1H, J=7), 4.51 (s, 2H), (5.16s + 5.21s)3H. |
| 29 | $C_2H_5N$—[ring]—NCONHCHCO—$C_2H_5$ | $CH_3O$ | O | $CH_3$ | H | Na | KBr: 3500-3300, 1770, 1710, 1680, 1608, 1518. | $D_2O$: 0.98(t, 3H, J=7), 1.19(t, 3H, J=7), 1.89(dq, 2H, J=7; 7), 3.49(t, 2H, J=7), 3.6-3.9(m, 2H), 3.55(s, 3H), 3.79(s, 3H), 4.0-4.2(m, 2H), 4.18(d, 1H, J=8), 4.28(d, 1H, J=8), 4.41(t, 1H, J=7), 4.51(s, 2H), (5.17s + 5.22s)3H. |
| 30 | Ph—CHCO—NH$_2$ | H | S | H | H | H | | $D_2O$: 3.70d + 4.08d(ABq, 2H, J=12), 5.47(d, 1H, J=5), 6.13(d, 1H, J=5), 5.70(s, 1H), 7.92(s, 5H). |

TABLE 1-continued

Structure:
$$RNH-\underset{R^1}{\overset{}{C}}-\text{(β-lactam with X)}-N-\underset{COOR^5}{\overset{CH_2S}{C}=C}-\overset{N=N}{\underset{N}{\underset{|}{N}}}-\underset{CH_2CON}{\overset{OR^3}{\underset{R^4}{}}}$$

| No. | R | R$^1$ | X | R$^3$ | R$^4$ | R$^5$ | IR | NMR |
|---|---|---|---|---|---|---|---|---|
| 31 | Ph-CH(NHCOOt-C$_4$H$_9$)-CHO | H | S | PMB | H | BH | CHCl$_3$: 3420,1785, 1710,1610. | CDCl$_3$: 1.40(s, 9H), 3.33–3.53(m, 2H), 3.70 (s, 3H), 4.03–4.30(m, 2H), 4.57–4.93 (m, 4H), 5.23(d, 1H, J=7), 5.53–5.93 (m, 2H), 6.85(s, 1H), 6.67–7.53(m, 22H). |
| 32 | 2-thienyl-CH(NHCONH$_2$)-CHO | CH$_3$O | O | CH$_3$ | H | H | KBr: 3380,1780, 1745,1690. | CD$_3$OD: 3.37(s, 3H), 3.47(s, 3H), 4.23(brs, 2H), 4.50(brs, 2H), 4.93(brs, 2H), 5.05(s, 1H), 5.70(s, 1H), 6.8–7.3(m, 13H). |
| 33 | 2-thienyl-CH(NHCONH$_2$)-CHO | CH$_3$O | O | CH$_3$ | H | BH | Nujol: 3450,3330, 1770,1700, 1660. | CDCl$_3$ + CD$_3$OD: 3.40(s, 3H), 3.50(s, 3H), 3.68(s, 3H), 4.20(brs, 2H), 4.48(brs, 2H), 4.93(brs, 2H), 5.08(s, 1H), 5.73(s, 1H), 6.8–7.0 (m, 13H). |
| 34 | 2-aminothiazol-4-yl-C(=NOCH$_3$)CO— | H | S | H | H | H | Nujol: 3200,1765, 1700,1690, 1670. | d$_6$-DMSO: 3.68(ABq, 2H, J=18), 3.83(s, 3H), 4.33(ABq, 2H, J=14), 4.98(s, 2H), 5.12(d, 1H, J=4), 5.75(dd, 1H, J=9,4.5), 6.74(s, 1H). |
| 35 | 2-aminothiazol-4-yl-C(=NOCH$_3$)CO— | H | S | CH$_3$ | H | H | Nujol: 3160,1770, 1705,1670, 1630. | d$_6$-DMSO: 3.65(s, 3H), 3.70(s, 2H), 3.85(s, 3H), 4.34(ABq, 2H, J=13.5), 5.03(brs, 2H), 5.12(d, 1H, J=4.5), 5.78(dd, 1H, J=9; 4.5), 6.74(s, 1H), 7.2(brs, 2H), 9.60(d, 1H, J=9). |
| 36 | 2-aminothiazol-4-yl-C(=NOCH$_3$)CO— | H | S | CH$_3$ | H | BH | CHCl$_3$: 3400,3225, 1790,1735, 1695. | CDCl$_3$ + CD$_3$OD: 3.36(brs, 2H), 3.65(s, 3H), 3.95(s, 3H), 4.20(brs, 2H), 4.80(brs, 2H), 5.03(d, 1H, J=4), 5.18(s, 2H), 5.88(d, 1H, J=4), 6.80(s, 2H), 6.9–7.5(m, 15H). |

TABLE 1-continued

![Structure: RNH-R¹ attached to β-lactam ring with X, connected to N, CH₂S, COOR⁵, with side chain =N-N-N-OR³ and CH₂CON(R⁴)]

| No. | R | R¹ | X | R³ | R⁴ | R⁵ | IR | NMR |
|---|---|---|---|---|---|---|---|---|
| 37 | ![N-aminothiazolyl C-CO= with NOCH₃, H₂N-] | H | S | PMB | H | BH | CHCl₃: 3370,3200, 1775,1720, 1680,1605. | CDCl₃ + CD₃OD(5:1): 3.63(brs, 2H), 3.73(s, 3H), 3.97(s, 3H), 4.22(brs, 2H), 4.75(s, 2H), 5.05(d, 1H, J=4.5), 5.22(s, 2H), 5.93(d, 1H, J=4), 6.79(s, 1H), 6.89(s, 1H), 7.2–7.6 (m, 19H). |
| 38 | ![aminothiazolyl C-CO= NOC(CH₃)₂COOH, H₂N-] | H | S | H | H | H | Nujol: 1777,1678. | d₆-DMSO + CD₃OD: 1.83(s, 6H), 3.95d + 4.18d(ABq, 2H, J=15), 5.36(s, 2H), 5.51(d, 1H, J=5), 6.19(d, 1H, J=5), 7.13(s, 1H). |
| 39 | ![aminothiazolyl C-CO= NOC(CH₃)₂COOH, H₂N-] | H | S | CH₃ | H | H | | CD₃OD: 1.61(s, 3H), 1.64(s, 3H), 3.68(s, 2H), 3.73(s, 3H), 4.27d + 4.46d(ABq, 2H, J=15), 5.06(brs, 2H), 5.17(d, 1H, J=5), 5.78(d, 1H, J=5), 6.90(s, 1H). |
| 40 | ![aminothiazolyl C-CO= NOC(CH₃)₂COOtC₄H₉, H₂N-] | H | S | CH₃ | H | BH | CHCl₃: 3400,1795, 1723,1690, 1250,1148. | CDCl₃: 1.93(s, 9H), 1.57(s, 3H), 1.59(s, 3H), 3.63(s, 2H), 3.69(s, 3H), 4.16d + 4.36d (ABq, 2H, J=14), 4.93(brs, 2H), 5.02(d, 1H, J=4.5), 5.97(dd, 1H, J=4.6; 9.0), 6.73 (s, 1H), 6.90(s, 1H), 7.33(m, 1H), 8.13(d, 1H, J=9). |
| 41 | ![aminothiazolyl C-CO= NOC(CH₃)₃, OCOtC₄H₉, Ph₃CNH-] | H | S | PMB | H | BH | CHCl₃: 3395,1790, 1720,1685, 1248. | CDCl₃: 1.41(s, 9H), 1.63(s, 6H), 3.63(brs, 2H), 3.75(s, 3H), 4.15d + 4.38d(ABq, 2H, J=15), 4.78(s, 2H + 2H), 5.02(d, 1H, J=5), 5.94(dd, 1H, J=5; 9), 6.76 (s, 1H), 6.91(s, 1H), 6.80–7.48(m, 8.15(d, 1H, J=9). |
| 42 | ![aminothiazolyl C-CO= NOC(CH₃)₂OCOtC₄H₉, Ph₃CNH-] | H | SO | CH₃ | H | BH | CHCl₃: 3375,1806, 1728,1698, 1250,1146. | CDCl₃: 1.38(s, 9H), 1.52(s, 6H), 3.56(s, 3H), 3.50d + 3.75d(ABq, 2H, J=16), 4.62(d, 1H, J=5), 4.89(bs, 2 + 2H), 6.13(dd, 1H, J=5; 10), 6.71(s, 1H), 6.93(s, 1H), 7.16–7.50(m), 7.78(d, 1H, J=10) |

TABLE 1-continued

[Structure: RNH-R¹ attached to β-lactam ring with X, connected to =C(COOR⁵)(CH₂S-C(=N-N=N-N-OR³)(R⁴)-CH₂CON...)]

| No. | R | R¹ | X | R³ | R⁴ | R⁵ | IR | NMR |
|---|---|---|---|---|---|---|---|---|
| 43 | [Ph₃CNH-C(=N)-S-C(=C-CO-NOC(CH₃)₂-t-BuOCO)] | H | SO | PMB | H | BH | CHCl₃: 3400,1805 1725,1690, 1257,1188. | CDCl₃: 1.40(s, 9H), 1.55(s, 6H), 3.40d + 3.75d(ABq, 2H, J=17), 3.72(s, 3H), 4.53(d, 1H, J=5), 4.73(brs, 2H + 2H + 2H), 6.08(dd, 1H, J=5; 9), 6.70(s, 1H), 6.90(s, 1H), 6.78–7.50(m, 1H), 7.78(d, 1H, J=9). |
| 44 | NC-CH=CH-SCH₂CO— | CH₃O | O | CH₃ | H | H | Nujol: 3451,3203, 2207,1775, 1680,1211, 1169. | |
| 45 | NC-CH=CH-SCH₂CO— | CH₃O | O | CH₃ | H | BH | CHCl₃: 3336,3249, 2218,1783, 1783,1700. | CDCl₃ + CD₃OD: 3.52(s, 5H), 3.66(s, 3H), 4.16(brs, 2H), 4.82(brs, 2H), 5.03(s, 1H), 5.32(d, J=10, 1H), 6.82(s, 1H), 7.0–7.7(m, 11 H). |
| 46 | Cl-CH=CH-SCH₂CO— | CH₃O | O | H | H | H | | CD₃COCD₃: 3.48(s, 3H), 3.61(s, 2H), 4.32(s, 2H), 4.63(s, 2H), 5.11(s, 1H), (5.11s + 5.43s)2H, 6.25(d, 1H, J=6), 6.75(d, 1H, J=6), 8.25(brs, 1H). |
| 47 | Cl-CH=CH-SCH₂CO— | CH₃O | O | CH₃ | H | H | Nujol: 3150,1770, 1660. | CD₃COCD₃: 3.50(s, 3H), 3.62(s, 2H), 3.78(s, 3H), 4.33(s, 2H), 4.63(s, 2H), 5.13(brs, 3H), 6.28(d, 1H, J=6), 6.71(d, 1H, J=6), 8.23(brs, 1H). |
| 48 | Cl-CH=CH-SCH₂CO— | CH₃O | O | C₂H₅ | H | H | Nujol: 3400,3100, 1770,1710, 1670. | CD₃COCD₃: 1.24(t, 3H, J=7), 3.50(s, 3H), 3.62(s, 2H), 4.00(q, 2H, J=7), 4.32(s, 2H), 4.63(s, 2H), 5.12(s, 3H), 6.25(d, 1H, J=6), 6.76(d, 1H, J=6), 8.23(brs, 1H). |
| 49 | Cl-CH=CH-SCH₂CO— | CH₃O | O | CH₃ | COOCH₃ | H | Nujol: 3300,1770, 1710,1690. | CD₃COCD₃: 2.82(s, 3H), 3.51(s, 3H), 3.56(s, 2H), 4.22d + 4.61d(ABq, 2H, J=13), 4.61(s, 2H), 5.12(s, 1H), 5.71(s, 2H), 6.23(d, 1H, J=6), 6.71(d, 1H, J=6). |

TABLE 1-continued

![Structure: RNH-R¹ on β-lactam with X, COOR⁵, CH₂S-thiadiazole-N(OR³)CH₂CON(R⁴)- type]

| No. | R | R¹ | X | R³ | R⁴ | R⁵ | IR | NMR |
|---|---|---|---|---|---|---|---|---|
| 50 | Cl-CH=CH-SCH₂CO— | CH₃O | O | CH₃ | H | BH | | CDCl₃ + CD₃OD: 3.42(s, 2H), 3.52(s, 3H), 3.67(s, 3H), 4.13(s, 2H), 4.53(s, 2H), 4.87(s, 2H), 5.05(s, 1H), 6.10(d, 1H, J=6), 6.50(d, 1H, J=6), 6.88(s, 1H), 7.2-7.8(m, 12H). |
| 51 | Cl-CH=CH-SCH₂CO— | CH₃O | O | C₂H₅ | H | BH | Nujol: 3150, 1775, 1670. | CDCl₃: 1.13(t, 3H, J=7), 3.42(s, 2H), 3.51(s, 3H), 3.87(q, 2H, J=7), 4.13(s, 2H), 4.52(s, 2H), 4.82(brs, 2H), 5.04(s, 1H), 6.10(d, 1H, J=6), 6.35(d, 1H, J=6), 6.88(s, 1H), 7.2-7.7(m, 10 H). |
| 52 | Cl-CH=CH-SCH₂CO— | CH₃O | O | i-C₃H₇ | H | BH | | CDCl₃ + CD₃OD: 1.20(d, 3H, J=7), 3.46(s, 2H), 3.56(s, 3H), 3.9-4.3(m, 1H), 4.21(s, 2H), 4.56(s, 2H), (4.87 + 5.15s)2H, 5.10(s, 1H), 6.12(d, 1H, J=6), 6.52(d, 1H, J=6), 6.90(s, 1H), 7.2-7.6(m, 10 H). |
| 53 | Cl-CH=CH-SCH₂CO— | CH₃O | O | PMB | H | BH | Nujol: 3170, 1670br. | CDCl₃ + CD₃OD: 3.43(s, 2H), 3.54(s, 3H), 3.75(s, 3H), 4.15(s, 2H), 4.53(s, 2H), 4.78(s, 4H), 5.06(s, 1H), 6.10(d, 1H, J=6), 6.50(d, 1H, J=6), 6.7-7.7(m). |
| 54 | Cl-CH=CH-SCH₂CO— | CH₃O | O | CH₃ | COOCH₃ | BH | | CDCl₃ + CD₃OD: 2.83(s, 3H), 3.45(s, 2H), 3.55(s, 3H), 4.23(s, 2H), 4.55(s, 2H), 5.08(s, 1H), 5.46(brs, 2H), 6.12(d, 1H, J=6), 6.52(d, 1H, J=6), 6.90(s, 1H), 7.2-7.7(m, 11H). |
| 55 | Cl-CH=CH-SCH₂CO— | CH₃O | O | i-C₃H₇ | H | Na | | D₂O: 1.70(s, 6H), 4.0(s, 3H), 4.07(s, 2H), 4.71(s, 2H), 4.3-4.7(m, 1H), 4.95(s, 2H), 5.63(s, 1H), 5.68(s, 2H), 6.71(d, 1H, J=6), 7.03(d, 1H, J=6). |
| 56 | Cl-CH=CH-SCH₂CO— | CH₃O | O | CH₃ | CO-O-CH₃ | BH | | CDCl₃: 3.42(s, 2H), 3.54(s, 3H), 3.76(s, 3 H), 4.41(s, 2H), 4.57(s, 2H), 4.99(s, 2H), 5.04(s, 1H), 5.13(s, 2H), 6.12d + 6.39(ABq, 2H, J=6), 6.92(s, 1H). |

TABLE 1-continued

Structure:

RNH-[R¹]-[β-lactam with X, N, CH₂S-C(=N-N=N-)-CONHOR³/R⁴ at 3-position and COOR⁵ at 4-position]

| No. | R | R¹ | X | R³ | R⁴ | R⁵ | IR | NMR |
|---|---|---|---|---|---|---|---|---|
| 57 | H₂NCO-C(Cl)=CH-SCH₂CO— | CH₃O | O | PMB | H | BH | CHCl₃: 3350,1790, 1710. | CDCl₃: 3.43(s, 5H), 3.70(s, 3H), 4.07(s, 2H), 4.33(s, 2H), 4.71(s, 4H), 4.98(s, 1H), 6.7–7.7(m, 14H), 8.0(s, 1H). |
| 58 | H₂NCO-C(Cl)=CH-SCH₂CO— | CH₃O | O | H | H | H | Nujol: 3200,1780, 1690. | CD₃COCD₃: 2.50(s, 3H), 3.86(s, 2H), 4.33(s, 2H), 4.63(s, 2H), 5.13(s, 1H), 5.13(brs, 1H), 5.45(brs, 1H), 8.16(s, 1H), 8.43(s, 1H). |
| 59 | [thiazine-CO—] | CH₃O | O | (3-CH₂Cl)*¹ | H | BH | CHCl₃: 3400,1790, 1720,1705, 1690. | CDCl₃: 3.54(s, 3H), 4.18(bs, 1H), 4.47(s, 2H), 4.51(s, 2H), 5.07(s, 1H), 5.50(d, J=6Hz, 1H), 6.23–6.45(m, 1H), 6.93(s, 1H), 7.23–7.63(m, 10H), 7.71(bs, 1H), 8.15(bs, 1H). |
| 60 | [thiazine-CO—] | CH₃O | O | CH₃ | H | BH | CHCl₃: 1790,1730. | CDCl₃: 3.57(s, 3H), 3.71(s, 3H), 4.20 (bs, 3H), 4.50(s, 2H), 4.85(bs, 2H), 5.04(s, 1H), 5.51(dd, J=3; 7Hz, 1H), 6.30(dd, J=3; 7Hz, 1H), 6.89(s, 1H), 7.25–7.63(m, 10H). |
| 61 | [thiazine-CO—] | CH₃O | O | CH₃ | H | H | KBr: 3450,3260, 1780,1690. | CDCl₃: 3.53(s, 3H), 3.75(s, 3H), 4.20 (m, 1H), 4.27(s, 2H), 4.56(s, 2H), 5.05(s, 3H), 5.61(dd, J=3; 7Hz, 1H), 6.36(dd, 3; 7Hz, 1H). |

Note *¹:
At columns R³ and R⁴ of Tables, (3-CH₂Cl) shows compounds represented by the following formula having the 3-chloromethyl group.

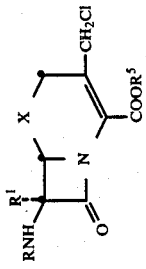

What we claim is:

1. A 7β-amino-3-[1-(N-hydroxyaminocarbonylalkyl)-1H-tetrazol-5-ylthiomethyl]-3-cephem-4-carboxylic acid derivative represented by the following formula:

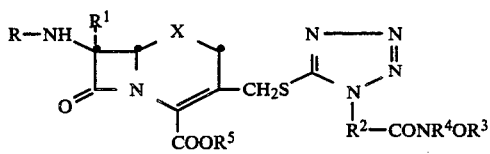

(wherein
R is hydrogen;
$R^1$ is hydrogen or methoxy;
$R^2$ is alkylene;
$R^3$ is hydrogen, alkyl, or a hydroxy-protecting group;
$R^4$ is hydrogen or an amino protecting group;
$R^5$ is hydrogen, a pharmaceutically acceptable salt forming group, or an ester forming group; and
X is oxygen.

2. A compound as claimed in claim 1 wherein $R^1$ is methoxy.

3. A compound as claimed in claim 1 wherein $R^2$ is lower alkylene.

4. A compound as claimed in claim 1 wherein $R^3$ is lower alkyl and $R^4$ is hydrogen.

5. A compound as claimed in claim 1 wherein $R^5$ is hydrogen or sodium.

6. A compound as claimed in claim 1 wherein $R^1$ is methoxy, $R^2$ is methylene and $R^4$ is hydrogen.

7. A compound as claimed in claim 1 wherein $R^1$ is methoxy, $R^2$ is methylene, $R^3$ is methyl, $R^4$ is carbobenzoxy and $R^5$ is diphenylmethyl.

* * * * *